US006476288B1

(12) United States Patent
VanRijswijck et al.

(10) Patent No.: US 6,476,288 B1
(45) Date of Patent: Nov. 5, 2002

(54) ABSORBENT ARTICLES HAVING CUFFS AND TOPSHEET WITH SKIN CARE COMPOSITION(S) DISPOSED THEREON

(75) Inventors: Laura Graves Spalding VanRijswijck, Burlington, KY (US); Gretchen Louise Elder, Blue Ash; Donald Carroll Roe, West Chester, both of OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/507,659

(22) Filed: Feb. 22, 2000

Related U.S. Application Data

(60) Division of application No. 08/962,312, filed on Oct. 31, 1997, now Pat. No. 6,120,488, and a continuation-in-part of application No. 08/908,852, filed on Aug. 8, 1997, and a continuation-in-part of application No. 08/884,069, filed on Jun. 27, 1997, now Pat. No. 6,118,041, which is a continuation-in-part of application No. 08/766,386, filed on Dec. 3, 1996, now Pat. No. 6,156,024, which is a continuation-in-part of application No. 08/345,159, filed on Nov. 28, 1994, now Pat. No. 5,643,588.

(51) Int. Cl.[7] .............................................. A61F 13/15
(52) U.S. Cl. ........................ 604/364; 604/359; 604/367; 604/360
(58) Field of Search .............................. 604/364, 385.25, 604/360, 359; 424/404, 402

(56) References Cited

U.S. PATENT DOCUMENTS

| 2,804,424 A | | 8/1957 | Stirn et al. |
| 3,489,148 A | * | 1/1970 | Duncan et al. ............ 128/284 |
| 3,490,454 A | | 1/1970 | Goldfarb et al. |
| 3,585,998 A | | 6/1971 | Hayford et al. |
| 3,814,101 A | | 6/1974 | Kozak |
| 3,860,003 A | | 1/1975 | Buell |
| 3,875,942 A | | 4/1975 | Roberts et al. |
| 3,896,807 A | * | 7/1975 | Buchalter ................ 128/261 |
| 3,902,493 A | | 9/1975 | Baier et al. |
| 4,034,077 A | | 7/1977 | Hill et al. |
| 4,112,167 A | | 9/1978 | Dake et al. |
| 4,263,363 A | | 4/1981 | Buck et al. |
| 4,324,247 A | | 4/1982 | Aziz |
| 4,478,853 A | | 10/1984 | Chaussee |
| 4,513,051 A | | 4/1985 | Lavash |
| 4,556,560 A | | 12/1985 | Buckingham |
| 4,569,343 A | | 2/1986 | Kimura et al. |
| 4,623,339 A | | 11/1986 | Ciraldo et al. |
| 4,666,765 A | | 5/1987 | Caldwell et al. |
| 4,690,821 A | | 9/1987 | Smith et al. |
| 4,695,278 A | | 9/1987 | Lawson |
| 4,704,112 A | | 11/1987 | Suzuki et al. |

(List continued on next page.)

FOREIGN PATENT DOCUMENTS

| CA | 2019557 A1 | 12/1990 |
| DE | 4136540 A1 | 5/1992 |
| EP | 0 297 828 A1 | 1/1989 |

(List continued on next page.)

*Primary Examiner*—John G. Weiss
*Assistant Examiner*—Jacqueline F. Sheets
(74) *Attorney, Agent, or Firm*—Kirsten K. Stone; Caroline Wei-Berk; Ken K. Patel

(57) ABSTRACT

An absorbent article, such as a diaper, containing cuffs and a topsheet with one or more skin care compositions disposed thereon. The skin care compositions are transferable to the wearer's skin by normal contact and/or wearer motion and/or body heat. The skin care compositions disclosed in the present invention are selected to maintain and/or improve the skin health of the wearer upon transfer during use, for example, to provide a skin protective barrier or a therapeutic benefit; to minimize the abrasion between the cuffs and skin in the area where the cuffs contact the wearer's skin, resulting in less skin irritation; to improve BM clean up on the skin, or to improve the barrier properties of the cuffs.

2 Claims, 7 Drawing Sheets

U.S. PATENT DOCUMENTS

| | | | |
|---|---|---|---|
| 4,753,643 A | 6/1988 | Kassai | |
| 4,760,096 A | 7/1988 | Sakai et al. | |
| 4,790,836 A | 12/1988 | Bracher | |
| 4,795,454 A | 1/1989 | Dragoo | |
| 4,834,737 A | 5/1989 | Khan | |
| 4,636,207 A | 11/1989 | Buell | |
| 4,882,204 A | 11/1989 | Tenenbaum | |
| 4,900,317 A | 2/1990 | Buell | |
| 4,904,524 A | 2/1990 | Yoh | |
| 4,909,803 A * | 3/1990 | Aziz et al. | 604/385.2 |
| 4,959,059 A | 9/1990 | Eilender et al. | |
| 4,970,220 A | 11/1990 | Chaussee | |
| 4,990,144 A | 2/1991 | Blott | |
| 4,996,238 A | 2/1991 | Matravers | |
| 5,026,364 A | 6/1991 | Robertson | |
| 5,043,155 A | 8/1991 | Puchalski et al. | |
| 5,110,593 A | 5/1992 | Benford | |
| 5,151,092 A | 9/1992 | Buell et al. | |
| 5,194,261 A | 3/1993 | Pichierri | |
| 4,589,876 A | 4/1993 | Van Tilburg | |
| 5,264,460 A | 11/1993 | Jakobson et al. | |
| 5,321,098 A | 6/1994 | Lal | |
| 5,354,425 A * | 10/1994 | Mackey et al. | 162/135 |
| 5,370,132 A | 12/1994 | Weber et al. | |
| 5,415,649 A | 5/1995 | Watanabe et al. | |
| 5,436,007 A | 7/1995 | Hartung et al. | |
| 5,466,396 A | 11/1995 | Madison et al. | |
| 5,509,915 A | 4/1996 | Hanson et al. | |
| 5,525,345 A * | 6/1996 | Warner et al. | 424/402 |
| 5,525,346 A * | 6/1996 | Hartung et al. | 424/402 |
| 5,558,655 A | 9/1996 | Jezzi et al. | |
| 5,569,230 A | 10/1996 | Fisher et al. | |
| 5,569,232 A | 10/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,582,605 A | 12/1996 | Lepie | |
| 5,607,760 A | 3/1997 | Roe | |
| 5,609,587 A | 3/1997 | Roe | |
| 5,624,676 A | 4/1997 | Mackey et al. | |
| 5,635,191 A | 6/1997 | Roe et al. | |
| 5,643,588 A | 7/1997 | Roe et al. | |
| 5,649,917 A | 7/1997 | Roberts et al. | |
| 5,656,591 A | 8/1997 | Tomita et al. | |
| 5,674,509 A | 10/1997 | Date et al. | |
| 5,753,245 A * | 5/1998 | Fowler et al. | 424/401 |
| 5,871,763 A | 2/1999 | Luu et al. | |
| 5,938,649 A | 8/1999 | Ducker et al. | |
| 6,107,537 A | 8/2000 | Elder et al. | |
| 6,120,488 A * | 9/2000 | VanRijswijck et al. | 604/385.2 |
| 6,120,783 A | 9/2000 | Roe et al. | |
| 6,166,285 A | 12/2000 | Schulte et al. | |
| 6,238,682 B1 * | 5/2001 | Klofta et al. | 424/402 |

FOREIGN PATENT DOCUMENTS

| | | |
|---|---|---|
| EP | 0 631 768 A1 | 1/1995 |
| EP | 0 692 263 B1 | 1/1996 |
| EP | 0 815 841 A1 | 1/1998 |
| GB | 2033751 A | 5/1980 |
| JP | 61-028078 | 2/1986 |
| JP | 02-31756 | 2/1990 |
| JP | 05-285170 | 11/1993 |
| JP | 08-52175 | 2/1996 |
| WO | WO 98/03147 | 1/1998 |

* cited by examiner

ABSORBENT ARTICLES HAVING CUFFS AND TOPSHEET WITH SKIN CARE COMPOSITION(S) DISPOSED THEREON

This is a divisional of Ser. No. 08/962,312, filed Oct. 31, 1997, now U.S. Pat. No. 6,120,488, continuation-in-part of application Ser. No. 08/766,386 filed on Dec. 3, 1996; now U.S. Pat. No. 6,156,024 and is a continuation-in-part of application Ser. No. 08/884,069 filed on Jun. 27, 1997, now U.S. Pat. No. 6,118,041 which is a continuation of application Ser. No. 08/345,159, filed on Nov. 28, 1994, now U.S. Pat. No. 5,463,588; and is a continuation-in-part of pending application Ser. No. 08/908,852 filed on Aug. 8, 1997.

TECHNICAL FIELD

The present invention relates to absorbent articles such as diapers, training pants, adult incontinence devices, sanitary napkins, feminine garments, and the like, having cuffs, including elastic leg cuffs. More particularly, the present invention relates to absorbent articles having a skin care composition disposed on the cuffs or the cuffs and the topsheet that is transferable to the wearer's skin by normal contact and/or wearer motion and/or body heat. The skin care compositions disclosed in the present invention are selected to maintain and/or improve the skin health of the wearer upon transfer during use, for example, to provide a skin protective barrier or a therapeutic benefit; to minimize the abrasion between the cuffs and skin in the area where the cuffs contact the wearer's skin, resulting in less red marking or skin irritation; to improve BM clean up on the skin, or to improve the barrier properties of the cuffs.

BACKGROUND OF THE INVENTION

The major function of absorbent articles such as disposable diapers and incontinent briefs or undergarments is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's legs or waist to adjacent clothing because they are not immediately absorbed within the article and the absorbent article is not able to sustain a good fit on the wearer such that gaps are created allowing the exudates to leak out of the article. For example, urine tends to be deposited onto the topsheet in gushes such that the urine migrates to the gaps between the article and the wearer where it can come in contact with clothing or other articles and be absorbed by these articles. Additionally, loose fecal material that is not easily absorbed by the absorbent article tends to "float" on the body-contacting surface and work its way past the gaps between the article and the legs or waist of the wearer.

Contemporary disposable diapers have a topsheet, a backsheet, an absorbent core, and one or more cuffs, typically elastic cuffs, positioned to contact the legs and/or waist of the wearer. These elastic cuffs prove effective generally to prevent wicking and overflow from the fluid laden diaper to clothing contacting the edges of the diaper in that the elastic cuffs present a barrier between the edge of the diaper and the contacting clothing, and generally in addition, provide a gasketing action about the legs or waist of the wearer to maintain a seal about the leg or waist and minimize gapping. However, because the forces generated by the elastic members are concentrated along a narrow area resulting in high localized pressures, such elastic cuffs have an increased tendency to indent and mark the skin of the wearer. These skin effects are particularly acute for products worn by infants and incontinent elderly adults due to the tenderness of their skin and its sensitivity to even slight pressures or rubbing actions. These skin effects are even further acute due to the occlusion of the skin caused by such products. The occlusion of the skin by the diaper can potentially lead to skin overhydration. As a result, overhydrated skin is more susceptible to damage from abrasion due to rubbing caused by normal wearer movements and contact with the elastic cuffs. It is also generally known that overhydrated skin is more susceptible to skin disorders, including diaper rash, erythema, heat rash, abrasion, pressure marks, and skin barrier loss. The reduced barrier efficiency of abraded, overhydrated skin can further cause an increase in diaper rash. (21 C.F.R. 333.503 defines diaper rash as "[a]n inflammatory skin condition in the diaper area (perineum, buttocks, lower abdomen, and inner thighs) caused by one or more of the following factors: moisture, occlusion, chafing, continued contact with urine or feces or both, or mechanical or chemical irritation.") To address the concerns of skin disorders associated with wearing diapers and other absorbent articles, the caregiver or wearer often applies skin protective and/or therapeutic products to the buttocks, genitals, anal and/or other regions before placing the absorbent article on the wearer. This procedure usually involves the caregiver applying the skin protective product to their hands, and then wiping the same on the skin of the wearer. To eliminate the need for this wasteful, messy, time-consuming, and easily forgotten procedure, there have been attempts to prepare absorbent articles which contain a skin care substance on the article's topsheet.

One substance that has been applied to diaper products to impart a soothing, protective coating is mineral oil. Mineral oil (also known as liquid petrolatum) is a mixture of various liquid hydrocarbons obtained by distilling the high-boiling (i.e., 300°–390° C.) fractions in petroleum. Mineral oil is liquid at ambient temperatures, e.g. 20°–25° C. As a result, mineral oil is relatively fluid and mobile when applied to diapers. Because mineral oil is fluid and mobile at ambient temperatures, it tends not to remain localized on the surface of the diaper, but instead migrates into the interior of the diaper. Accordingly, relatively high levels of mineral oil need to be applied to the diaper to provide the desired therapeutic or protective coating benefits. This leads not only to increased costs for these treated diaper products, but other detrimental effects as well, including decreased absorbency of the underlying absorbent core.

Even without increasing its level, the tendency of mineral oil to migrate once applied has other detrimental effects. For example, the applied mineral oil can transfer to, into and through the packaging or wrapper material for the treated diaper product. This can create the need for barrier-type packaging or wrapper films to avoid smearing or other leakage of mineral oil from the diaper product.

U.S. Pat. No. 3,489,148 to Duncan, et al. teaches a baby diaper comprising a hydrophobic and oleophobic topsheet wherein a portion of the topsheet is coated with a discontinuous film of oleaginous material. A major disadvantage of the diapers disclosed in the Duncan et al. reference is that the hydrophobic and oleophobic topsheets are slow in promoting transfer of urine to the underlying absorbent cores.

In addition to the migration problems encountered by placing liquid compositions on the topsheet, the prior art has failed to recognize the skin care detriments caused by the use of cuffs, nor of a way to treat the cuffs so that skin care compositions disposed thereon remain on the cuff and transfer to the wearer's skin in an effective amount to provide a skin care benefit. The prior art has also failed to recognize that treatment of an article's topsheet alone does not necessarily transfer the composition to all critical regions of the wearer's skin.

Thus, it would be desirable to provide an absorbent article having cuffs wherein a skin care composition is disposed on the cuffs to provide improved skin care benefits, particularly in skin regions in contact with the wearer during use. The skin care composition must be transferable to the wearer's skin to provide these skin benefits, as well as not inhibiting the functionality of the cuff in the product.

Accordingly, it would be desirable to provide diaper products or other absorbent articles having one or more cuffs with a skin care composition disposed thereon that: (1) have desirable therapeutic or protective coating benefits; and/or (2) do not require relatively high levels of skin care compositions that are liquid at room temperature (e.g., mineral oil); and/or (3) do not adversely affect the absorbency of the diaper product; and/or (4) do not necessarily require special wrapping or barrier materials for packaging.

Therefore, it is an object of the present invention to provide a diaper or absorbent article having one or more cuffs with a skin care composition disposed thereon, wherein at least a portion of the composition is transferable to the wearer's skin to provide desirable skin care benefits, including less skin irritation, less red marking, therapeutic benefits including a reduction in erythema and/or diaper rash, and/or reducing the adherence of BM to the skin, thereby improving the ease of BM cleanup. It is another object of the present invention to improve the containment/barrier function of cuffs when hydrophobic skin care compositions are used.

These and other objects are obtained using the present invention, as will become readily apparent from a reading of the following disclosure.

SUMMARY OF THE INVENTION

The present invention relates to an absorbent article, such as a disposable diaper, having one or more cuffs with a skin care composition disposed on (applied or migratable to) the body surface of the cuffs. Importantly, the skin care compositions useful herein are readily transferable to the wearer's skin by way of normal contact, wearer motion, and/or body heat. Upon transfer to the skin, the skin care composition provides desirable therapeutic and/or protective coating benefits resulting in less red marking, erythema, diaper rash, skin irritation, and/or reducing the adherence of BM to the skin of the wearer, thereby improving the ease of BM clean up. Where hydrophobic skin care compositions are employed, the skin care compositions described herein can also increase the containment/barrier properties of the cuffs, thereby improving their leakage protection. Such a hydrophobic skin care composition particularly allows for flexibility in cuff designs using nonwoven materials by providing an alternate method to achieve the desired containment/barrier properties. This can lead to reduced material costs.

As used herein, the term "cuff" includes leg cuffs including barrier cuffs, gasketing cuffs, combinations and variations thereof; transverse barriers and pockets/spacers; side panels; as well as waist cuffs including waist flaps, waistbands, waistcaps, and unitary waistcap/waistbands; and combinations of all or some of these cuffs.

Importantly, the skin care compositions described herein provide a protective and/or a therapeutic benefit upon transfer to the wearer's skin, including reducing erythema and/or diaper rash. The skin care composition may also act to minimize the abrasion between the cuffs and skin in the area where the cuffs contact the wearer's skin, resulting in less redmarking and/or skin irritation. Additionally, the protective coating on the wearer's skin may reduce the adherence of BM to the skin, thereby improving the ease of BM cleanup.

As will be discussed hereinafter, skin care compositions useful in the present invention preferably have a melting profile such that they are relatively immobile and localized on the cuffs at room temperature, are transferable to the wearer at body temperature, and yet are not completely liquid under extreme storage conditions. In such embodiments, less skin care composition is needed to impart the desired skin care benefits. In addition, special barrier or wrapping materials may not be necessary in packaging the treated products of the present invention.

In one preferred embodiment, an absorbent article of the present invention will comprise a skin care composition disposed on (applied or migratable to) the cuffs and the topsheet. Applicants have discovered that such preferred articles increase transfer of the composition to the wearer's skin, resulting in increased therapeutic and/or protective benefits discussed herein. In this regard, increased transfer will be realized as increased skin coverage (i.e., area of skin) and/or the amount of composition transferred to a given area of skin.

DETAILED DESCRIPTION OF THE INVENTION

Figure 1:
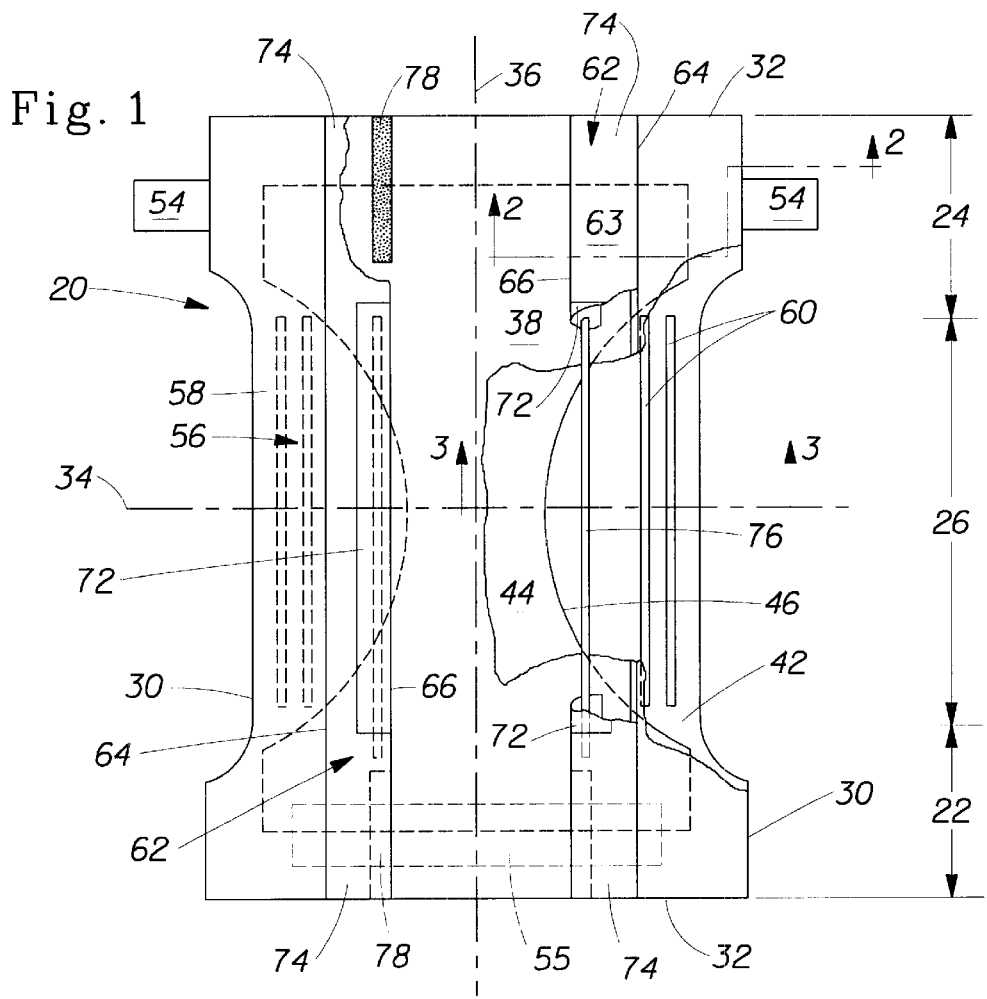
FIG. 1 is a plan view of a disposable diaper embodiment of the present invention having portions cut away to reveal underlying structure.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, the term "skin care composition" refers to any composition which comprises one or more agents which, when transferred from an article to a wearer's skin, provide a therapeutic and/or protective skin benefit. Representative materials are discussed in detail below.

All percentages, ratios and proportions used herein are by weight unless otherwise specified.

A. Absorbent Article

As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use. Examples of disposable absorbent articles include feminine hygiene products such as sanitary panties, sanitary napkins, and pantiliners; diapers; incontinence products such as briefs or undergarments; diaper holders; diaper inserts; pull-on diapers and training pants; and the like.

Disposable absorbent articles typically comprise a chassis comprising an outer covering layer comprising a liquid pervious topsheet and a liquid impervious backsheet joined to the topsheet, and an absorbent core encased within the outer covering layer, preferably being positioned between the topsheet and the backsheet. Disposable absorbent articles and components thereof, including the topsheet, backsheet, absorbent core, and any individual layers of these components, have two major surfaces (a first surface and a second surface) generally designated a body surface and a garment surface. As used herein, "body surface" (also referred to as the body-contacting surface or skin-contacting surface) means that surface of the article or component which is intended to be worn toward or adjacent to the body of the wearer, while the "garment surface" is on the opposite side that faces away from the wearer and is oriented toward the wearer's garments when the disposable absorbent article is worn.

The following description generally discusses the absorbent core, topsheet, and backsheet materials that are useful in disposable absorbent articles. It is to be understood that this general description applies to these components of the specific absorbent articles shown in FIGS. 1–4 and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, symmetric, asymmetric, etc.). In addition to the absorbent composites of the present invention, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones and/or have a profile so as to be thicker in the center; hydrophilic gradients; gradients of the absorbent composite, e.g., superabsorbent gradients; lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, training pants, pantiliners, regular sanitary napkins, and overnight sanitary napkins, and to accommodate wearers ranging from infants to adults.

The absorbent core can include other absorbent components that are often used in absorbent articles, for example, a dusting layer, a wicking or acquisition layer (surge management layer), or a secondary topsheet for increasing the wearer's comfort.

The topsheet is preferably compliant, soft feeling, and non-irritating to the wearer's skin. Further, the topsheet is liquid pervious, at least in certain regions, and permits liquids (e.g., menses and/or urine) to readily penetrate through its thickness. A suitable topsheet may be manufactured from a wide range of materials such as woven and nonwoven materials (e.g., a nonwoven web of fibers), including apertured nonwovens; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers), bicomponent fibers, or from a combination of natural and synthetic fibers. When the topsheet comprises a nonwoven web, the web may be manufactured by a wide number of known techniques. For example, the web may be spunbonded, carded, wet-laid, melt-blown, hydroentangled, hydroformed, hydroapertured, combinations of the above, or the like.

The backsheet is preferably impervious to liquids (e.g., menses and/or urine), at least in the crotch region of the absorbent article, and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a coated nonwoven or a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet is preferably embossed and/or matte finished to provide a more clothlike appearance. Further, the backsheet may permit vapors to escape from the absorbent core (i.e., the backsheet is breathable) while still preventing exudates from passing through the backsheet. (An example of a breathable backsheet suitable for use herein is disclosed in U.S. Pat. No. 5,571,096, "Absorbent Article Having Breathable Side Panels", issued to Dobrin, Davis and Weirich on Nov. 5, 1996, which patent is incorporated herein by reference.) The size of the backsheet is dictated by the size of the absorbent core and the exact absorbent article design selected.

The backsheet and the topsheet are positioned adjacent the garment surface and the body surface, respectively, of the absorbent core. The absorbent core is preferably joined with the topsheet, the backsheet, or both in any manner as is known by attachment members such as those well known in the art. However, embodiments of the present invention are envisioned wherein portions of the entire absorbent core are unattached to either the topsheet, the backsheet, or both.

The backsheet and/or the topsheet may be secured to the absorbent core or to each other, for example, by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment members will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

A preferred disposable absorbent article in which the "treated cuffs" ("treated cuffs" being used herein to designate cuffs having one or more skin care compositions disposed thereon) of the present invention may be used is a diaper. As used herein, the term "diaper" refers to an absorbent article generally worn by infants and incontinent persons that is worn about the lower torso of the wearer. In other words, the term "diaper" includes infant diapers, training pants, adult incontinence devices, and the like. The present invention is also applicable to other types of disposable products such as sanitary napkins and pantiliners that contain cuffs.

FIG. 1 is a plan view of a preferred embodiment of a diaper 20 of the present invention in its flat-out, uncontracted state (i.e., with all elastic induced contraction pulled out) with portions of the structure being cut away to more clearly show the construction of the diaper 20 and with the portion of the diaper 20 which contacts the wearer (the body surface) facing the viewer. The diaper 20 is shown in FIG. 1 to have a front waist region 22, a back waist region 24, a crotch region 26, and a periphery which is defined by the outer edges of the diaper in which the longitudinal edges are designated 30 and the end edges are designated 32. The diaper 20 additionally has a lateral centerline which is designated 34 and a longitudinal centerline which is designated 36. The diaper 20 comprises a chassis comprising (i) an outer covering layer comprising a liquid pervious topsheet 38 and a liquid impervious backsheet 42, and (ii) an absorbent core 44 having side edges 46; a fastening system preferably comprising a pair of tape-tab fasteners 54 and a landing member 55; gasketing cuffs 56 each comprising a side flap 58 and flap elastic members 60; barrier cuffs 62 comprising a barrier cuff member 63 having a proximal edge 64, a distal edge 66, and ends 74; and spacing means such as a spacing elastic member 76 for spacing the distal edge 66 away from the topsheet. The diaper 20 additionally comprises closure members 78 for securing closed the ends 74 of each barrier cuff 62. While the components of the diaper may be assembled in a variety of well known configurations, a preferred diaper configuration is described generally in U.S. Pat. No. 4,695,278 issued to Lawson on Sep. 22, 1987, and which patent is incorporated herein by reference.

FIG. 1 shows a preferred embodiment of the diaper 20 in which the topsheet 38 and the backsheet 42 are coextensive and have length and width dimensions generally larger than those of the absorbent core 44. The topsheet 38 is joined with and superposed on the backsheet 42 to thereby form the periphery of the diaper 20.

The diaper 20 has front and back waist regions 22 and 24 extending, respectively, from the end edges 32 of the periphery toward the lateral centerline 34 of the diaper 20. The waist regions comprise those portions of the diaper 20 which, when worn, encircle the waist of the wearer. The crotch region 26 is that portion of the diaper 20 between the waist regions and comprises that portion of the diaper 20 which, when worn, is positioned between the legs of the wearer and covers the lower torso of the wearer.

As shown in FIG. 1, a skin care composition 72 is disposed on each barrier cuff 62. The skin care composition 72 is preferably disposed on the body surface of the barrier cuff so that the skin care composition may readily transfer to the wearer's skin during use. In the embodiment shown, the skin care composition 72 is disposed adjacent the distal edge 66, preferably at least in the crotch region 26. More preferably, the skin care composition 72 is disposed on the distal edge 66. The barrier cuff 62 most preferably comprises one or more stripes of skin care composition 72 disposed thereon. In the embodiment shown, the skin care composition 72 is disposed on only a segment of the barrier cuff 62. For certain skin care compositions, it is preferred to avoid application of the skin care composition to the portions of the barrier cuff adjacent the ends of the spacing elastic members to insure there is no elastic creep resulting from the interaction of the skin care composition and adhesive. As is shown in FIG. 1, in a preferred embodiment the skin care composition 72 is not disposed adjacent the end of the spacing elastic member 76 in the front waist region (although it may alternatively also not be disposed adjacent the end in the back waist region). (Alternatively, an adhesive compatible with the skin care composition may be utilized such that placement of the skin care composition on the cuff is not restricted relative to the ends of the spacing elastic members.) As discussed herein, the skin care composition may alternatively be applied to the garment surface of the barrier cuff and allowed to "transfer through" to the body surface so as to enhance the hydrophobicity of the barrier cuffs as well as to be disposed on the body surface so as to provide the skin care benefits. Further, the skin care composition may be applied to other portions of the barrier cuff, the entire barrier cuff, the spacing elastic members, or any other component of the barrier cuff. The skin care composition may also be disposed in any pattern, including discontinuous or continuous patterns, or in any amount as discussed hereinafter.

Figure 2:
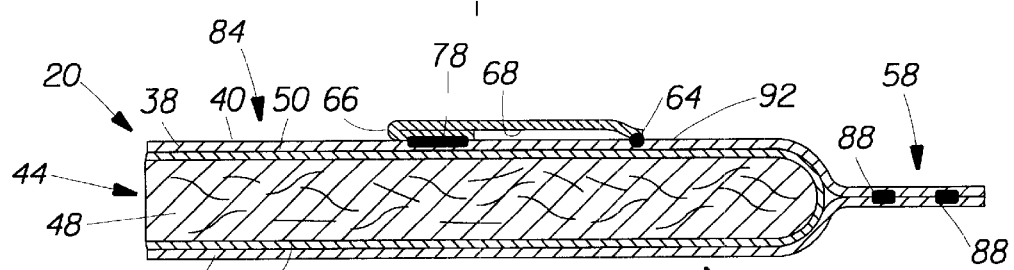
FIG. 2 is a fragmentary sectional view taken along section line 2—2 of FIG. 1.

The diaper 20 is shown in FIG. 2 to have a garment surface 86 and a body surface 84 opposed to the garment surface 86. The body surface 84 of the diaper 20 comprises that portion of the diaper 20 which is positioned adjacent to the wearer's body during use (i.e., the body surface 84 generally is formed by at least a portion of the topsheet 38 and other components including those that may be joined to the topsheet 38). The garment surface 86 comprises that portion of the diaper 20 which is positioned away from the wearer's body during use (i.e., the garment surface 86 generally is formed by at least a portion of the backsheet 42 and other components including those that may be joined to the backsheet 42).

FIG. 2 is a fragmentary sectional view taken along line 2—2 of FIG. 1 and depicts the diaper construction in the back waist region 24 of the diaper 20. (It should be understood that the diaper construction in the front waist region 22 is substantially identical to the construction in the back waist region 24.) The absorbent core comprises an absorbent layer 48 that is shown as being completely enveloped by tissue layers 50 and 52. The absorbent core 44 is disposed between the topsheet 38 and the backsheet 42; both the topsheet 38 and the backsheet 42 extend beyond the side edge 46 of the absorbent core 44 to define the side flap 58. The juxtaposed areas of the topsheet 38 and the backsheet 42 are secured together preferably by a flap attachment member 88 such as an adhesive. In a preferred embodiment, the flap elastic members do not extend into the back waist region 24 so that the gasketing cuff is not formed in this region. The barrier cuff 62 is shown as comprising a separate element, a barrier cuff member 63, secured to the topsheet 38; the proximal edge 64 being formed by securing the barrier cuff member 63 to the topsheet 38 by proximal securement member 92. The garment surface 68 of the barrier cuff 62 (also referred to as the barrier cuff's inboard surface) is secured to the body surface 40 by the closure member 78. Therefore, the distal edge 66 is closed. (i.e., it is not spaced away from the body surface 40). It should be noted that the spacing elastic member is not disposed in this region because the distal edge 66 is not designed to be spaced away from the body surface 40 in the waist regions. Therefore, the barrier cuff 62 is not open nor ready to constrain the flow of body exudates in this region. The skin care composition also is preferably not disposed on the barrier cuff in the back waist region in this particular embodiment.

Figure 3:
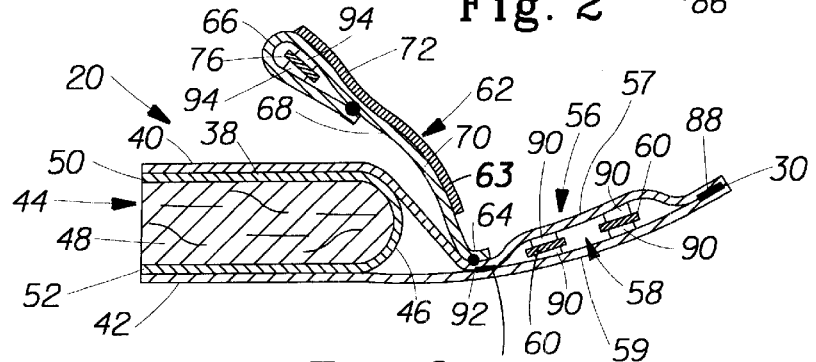
FIG. 3 is a fragmentary sectional view taken along section line 3—3 of FIG. 1.

FIG. 3 is a fragmentary sectional view taken along line 3—3 of FIG. 1 and depicts the diaper construction in the crotch region 26 as it is shaped before being applied to the wearer (i.e., the diaper 20 is subjected to elastic contraction). The absorbent core 44 comprises the absorbent layer 48 that is shown as being completely enveloped by the tissue layers 50 and 52. The absorbent core 44 is disposed between the topsheet 38 and the backsheet 42; both the topsheet 38 and the backsheet 42 extend beyond the side edge 46 of the absorbent core 44 to define the side flap 58. The juxtaposed areas of the topsheet 38 and the backsheet 42 are secured together preferably by a flap attachment member 88 such as an adhesive. The topsheet 38 and the backsheet 42 also enclose the flap elastic members 60 adjacent the longitudinal edge 30. The flap elastic members 60 are secured in the topsheet-backsheet formed side flap 58 preferably by elastic attachment members 90. The elastically contractible gasketing cuff 56 is thereby formed by the side flap 58 and the flap elastic members 60. The gasketing cuff has a body surface 57 oriented toward the skin of the wearer when the diaper is worn, and a garment surface 59 opposed to the body surface 57. The barrier cuff 62 is shown as being formed by securing a separate element, barrier cuff member 63, to the topsheet 38 preferably between the flap elastic members 60 and the side edge 46 of the absorbent core 44. The proximal edge 64 of the barrier cuff 62 is formed by securing the barrier cuff member 63 to the topsheet 38 by the proximal securement member 92. The spacing elastic member 76 is enclosed in a tunnel that is formed when an end of the barrier cuff member 63 is folded back upon itself; the spacing elastic member 76 being secured in the tunnel by elastic attachment members 94. The distal edge 66 of the barrier cuff is spaced away from the body surface 40 by the elastic gathering action of the spacing elastic member 76. The barrier cuff 62 is shown as being ready to restrain, contain and hold body exudates until the diaper 20 is removed from the wearer. The skin care composition 72 is shown in FIG. 3 as being disposed on the body surface 70 of the barrier cuff 62 (the barrier cuff element 63) so that the skin care composition 72 may be transferred to the skin of the wearer during use.

Diapers of the present invention can have a number of well known configurations, with the absorbent cores thereof being adapted to the present invention. Exemplary configurations are described generally in U.S. Pat. No. 3,860,003 issued to Buell on Jan. 14, 1975; U.S. Pat. No. 5,151,092 issued to Buell et al. on Sep. 29, 1992; U.S. Pat. No. 5,580,411 issued to Nease, et al. on Dec. 3, 1996; U.S. Pat. No. 5,569,232 issued to Roe, et al. on Oct. 29, 1996; and U.S. Pat. No. 5,569,234 issued to Buell, et al. on Oct. 29, 1996. Each of these patents is incorporated herein by reference.

The chassis of the diaper is shown in the drawings as comprising the main body portion (containment assembly) of the diaper. The chassis comprises at least an absorbent core and preferably an outer covering layer comprising the topsheet and the backsheet. When the absorbent article comprises a separate holder and a liner, the chassis generally comprises the holder and the liner (i.e., the chassis comprises one or more layers of material to define the holder while the liner comprises an absorbent composite such as a topsheet, a backsheet, and an absorbent core.) For unitary absorbent articles, the chassis comprises the main structure of the diaper with other features added to form the composite diaper structure; thus, the chassis for the diaper comprises the topsheet, the backsheet, and the absorbent core.

A topsheet 38 which is particularly suitable for use in the diaper 20, is carded and thermally bonded by means well known to those skilled in the fabrics art. A satisfactory topsheet for the present invention comprises staple length polypropylene fibers having a denier of about 2.2 As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8. An alternative preferred topsheet is a spunbonded nonwoven web of 22 grams per square meter basis weight as is available from Fiberweb North America, Inc. of Simpsonville, S.C., under the designation 9694.

The topsheet 38 of diaper 20 is preferably made of a hydrophilic material to promote rapid transfer of liquids (e.g., urine) through the topsheet. If the topsheet is made of a hydrophobic material, preferably at least the body surface of the topsheet, or a portion thereof, is treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated herein by reference.

In a particularly preferred embodiment as described herein, the topsheet of the absorbent article will also have a skin care composition disposed thereon. Representative treated topsheets are described in U.S. Pat. No. 5,643,588, "Diaper Having a Lotioned Topsheet", issued to Roe, Bakes & Warner on Jul. 1, 1997; and U.S. Pat. No. 5,635,191, "Diaper Having a Lotioned Topsheet Containing a Polysiloxane Emollient", issued to Roe & Mackey on Jun. 3, 1997; each of which are incorporated herein by reference. Methods for delivering a skin care composition via the repeated use of absorbent articles having such treated topsheets are disclosed in U.S. patent application Ser. No. 08/926,532 "A Method For Maintaining or Improving Skin Health", Elder, et al., filed on Sep. 10, 1997; U.S. patent application Ser. No. 08/926,533 "A Method For Improving Skin Condition", Van Rijswijck, et al. filed on Sep. 10, 1997; and U.S. patent application Ser. No. 08/908,852 "Diaper Having A Lotioned Topsheet", Roe, et al. filed on Aug. 8, 1997; each of which is incorporated herein by reference. As discussed herein, a skin care composition disposed on both the cuffs and the topsheet will facilitate transfer of the skin care composition to a greater amount of skin, in terms of surface area, relative to treatment of the cuffs only. Furthermore, application to both components may allow delivery of greater amounts of skin care composition to a given region of the wearer and/or delivery of different formulation skin care compositions for different skin benefits.

In a preferred embodiment of a diaper as described herein, the backsheet 42 has a modified hourglass shape extending beyond the absorbent core around the entire diaper periphery. The backsheet is preferably a soft, cloth-like web laminate comprising a selectively apertured polymeric formed film and a nonwoven web. Such a breathable backsheet is more fully described in U.S. Pat. No. 5,571,096 issued to Dobrin, et al. on Nov. 5, 1996, which patent is incorporated herein by reference.

The absorbent core 44 may take on any size or shape that is compatible with the diaper 20. One preferred embodiment of the diaper 20 has an asymmetric, modified T-shaped absorbent core 44 having ears in the first waist region but a generally rectangular shape in the second waist region. Exemplary absorbent structures for use as the absorbent core of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; EP Pat. No. Application 640 330, The Procter & Gamble Company, published Mar. 1, 1995; and U.S. Pat. No. 4,834,735, entitled "High Density Absorbent Members Having Lower Density and Lower Basis Weight Acquisition Zones", issued to Alemany et al. on May 30, 1989. The absorbent core may further comprise a dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

In a preferred embodiment, the diaper 20 comprises cuffs each comprising a leg cuff comprising a barrier cuff 62 and/or a gasketing cuff 56 for providing improved containment of liquids and other body exudates. The cuffs provide for improved containment of liquids and other body exudates and can be constructed in a number of different configurations. The diaper 20 may also comprise cuffs comprising an elastic waist feature (not shown) and/or elastic side panels (not shown) to provide a more contouring fit and more effective application of the diaper 20. Such cuffs may also be treated with a skin care composition.

Each leg cuff may comprise several different embodiments for reducing the leakage of body exudates in the leg regions. (The leg cuff can be and is sometimes also referred to as leg bands, side flaps, barrier cuffs, elastic leg cuffs, gasketing cuffs, or elastic cuffs.) U.S. Pat. No. 3,860,003, incorporated herein by reference, describes a disposable diaper which provides a contractible leg opening having a side flap and one or more elastic members to provide an elastic leg cuff (gasketing cuff). U.S. Pat. No. 4,909,803 entitled "Disposable Absorbent Article Having Elasticized Flaps" issued to Aziz et al. on Mar. 20, 1990, and incorporated herein by reference, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, and incorporated herein by reference, describes a disposable diaper having dual cuffs including a gasketing cuff and a barrier cuff. While each leg cuff may be configured so as to be similar to any of the leg bands, side flaps, barrier cuffs, or elastic cuffs described above, it is preferred that each leg cuff comprise barrier cuffs 62 and gasketing cuffs 56 as described in detail below.

Each barrier cuff 62 is a flexible member having a proximal edge 64, a distal edge 66, a garment surface 68 (also referred to as the inboard surface) and a body surface 70 (also referred to as the outboard surface). The garment surface 68 is oriented toward the interior of the diaper, and the body surface 70 is oriented toward the skin of the wearer when the diaper is being worn. The barrier cuff 62 may be manufactured from a wide variety of materials such as polypropylene, polyester, rayon, nylon, foams, nonwovens, plastic films, formed films, and elastic films or foams. A number of manufacturing techniques may be used to manufacture the barrier cuff. For example, the barrier cuff 62 may be woven, non-woven, spunbonded, spunbonded-meltblown-spunbonded, carded, coated, laminated or the like. A preferred barrier cuff 62 comprises a polypropylene material containing no finish or surfactant to render it liquid impermeable. An exemplary polypropylene fiber nonwoven material is manufactured by Crown Zellerbach Company as Celestra. A particularly preferred nonwoven material is a carded nonwoven web as is available from PGI of Landisville, N.J. under the designation 67700. Alternatively, the material may be a nonwoven web supplied by Corovin GmbH of Peine, Germany under the designation MD300A. In addition, because of the hydrophobic skin care compositions used in the present invention, the barrier cuff may be made from hydrophilic material and have a hydrophobic skin care composition disposed thereon to enhance its barrier properties.

As shown in FIGS. 1 and 3, the barrier cuff 62, and more particularly the proximal edge 64, is disposed inboard of the longitudinal edge 30, adjacent to and preferably inboard of the gasketing cuff 56. The term "inboard" is defined as the direction toward the centerline (34 or 36, respectively) of the diaper that is parallel to the respective edge of the diaper along which the particular gasketing cuff is disposed. The barrier cuff 62 is disposed adjacent the gasketing cuff 56 to provide a more effective dual restraint against the flow of body exudates. The barrier cuff 62 is preferably disposed inboard of the gasketing cuff 56 so that exudates, especially loose fecal material which is not easily absorbed and tends to float along the body surface 40, will contact the barrier cuff 62 before it can contact the gasketing cuff 56. The barrier cuff 62 is more preferably disposed between the flap elastic member 60 of the gasketing cuff 56 and the longitudinal centerline 36 of the diaper 20. Most preferably, the barrier cuff 62 is disposed between the flap elastic member 60 and the side edge 46 of the absorbent core 44 in the crotch region 26 of the diaper 20.

The proximal edge 64 and the distal edge 66 are in spaced relation to each other and define the width of the barrier cuff 62. The proximal and distal edges 64 and 66, respectively, may be in a parallel, non parallel, rectilinear or curvilinear relationship. In addition, the barrier cuff 62 may have a variety of different cross sectional areas including circular, square, rectangular or any other shape such as shown in FIG. 3. Preferably, the proximal edge 64 is spaced from the distal edge 66 in a parallel and rectilinear relationship to provide a barrier cuff 62 having uniform widths.

A preferred embodiment of the diaper 20 shown in FIGS. 2 and 3 is provided with the barrier cuff 62 joined to the topsheet 38. The term "joined" includes any means for affixing the barrier cuff 62 to the diaper 20, and includes embodiments wherein the barrier cuff 62 is a separate element having the proximal edge 64 directly or indirectly attached to the topsheet 38 (i.e., integral) or embodiments wherein the barrier cuff 62 is made from the same element or material as the topsheet 38 so that the proximal edge 64 is a continuous and undivided element of the topsheet (i.e., unitary). The barrier cuff 62 may alternatively be joined to the side flap 58, the backsheet 42, the absorbent core 44, the topsheet 38 or any combination of these or other elements of the diaper 20. In a preferred diaper 20, the barrier cuffs 62 are integral with the topsheet 38. The integral barrier cuff 62 is preferably formed by a strip of material, barrier cuff member 63, which is secured to the topsheet by proximal securement member 92, the distal edge 66 being formed by folding an end of the barrier cuff member 63 back upon itself.

The distal edge 66 is preferably disposed inboard of the proximal edge 64 to present a more effective barrier against the flow of exudates. The distal edges 66 are maintained inboard of the proximal edges 64 by the closure members 78 so as to obviate their inversion. While the distal edges 66 may alternatively be disposed in other positions in relation to the proximal edges 64, such positions are not preferred.

The distal edge 66 is preferably not secured to any other element in at least the crotch region 26 of the diaper 20 so that it may be spaced away from the body surface 40 of the topsheet 38. The distal edge 66 is preferably spaced away from the body surface 40 to enhance the containment of the article. As used herein, "spaced" includes embodiments wherein the distal edges 66 may assume one or more positions relative to the body surface 40 of the topsheet 38 including at some times assuming a position adjacent the body surface 40 of the topsheet 38. The distance between the distal edge 66 to the body surface 40 of the topsheet 38 is measured along a line drawn from the distal edge 66 to the closest part of the topsheet 38 when the distal edge 66 is positioned so as to be spaced away from the topsheet as far as possible. (i.e., in the elastically contracted position).

In addition to barrier cuffs, the leg cuffs of the present invention preferably further comprise gasketing cuffs 56. The gasketing cuffs 56 are disposed adjacent the periphery of the diaper 20, preferably along each longitudinal edge 30 so that the gasketing cuffs 56 tend to draw and hold the diaper 20 against the legs of the wearer. While the gasketing cuffs 56 may comprise any of several means as are well known in the diaper art, a particularly preferred gasketing cuff construction comprises a flexible side flap 58 and flap elastic members 60, as is described in detail in U.S. Pat. No. No. 3,860,003, issued to Buell on Jan. 14, 1975 and incorporated herein by reference. In addition, a method and apparatus suitable for manufacturing a disposable diaper having elastic gasketing cuffs 56 are described in U.S. Pat. No. 4,081,301 entitled "Method and Apparatus for Continuously Attaching Discrete, Stretched Elastic Strands to Predetermined Isolated Portions of Disposable Absorbent Articles" which issued to Buell on Mar. 28, 1978 and which patent is incorporated herein by reference.

The side flap 58 should be highly flexible and thus contractible so that the flap elastic members 60 may gather the side flap 58 to provide a gasketing cuff 56 about the legs or waist of the wearer. The side flaps 58 are preferably that portion of the diaper 20 between the periphery and the edges of the absorbent core 44. Thus, in a preferred embodiment of the present invention as shown in FIG. 1, the side flaps 58 are formed from the extension of the backsheet 42 and the topsheet 38 from and along the side edges 46 of the absorbent core 44 of the diaper 20 in at least the crotch region 26. Alternatively, as described in U.S. Pat. No. 3,860,003, the side flap may be a separate member joined to the chassis (topsheet, backsheet, and/or absorbent core) or one of the components of the side flap may be a separate member.

The flap elastic members 60 are preferably operatively joined (secured) to the side flaps 58 in an elastically contractible condition so that in a normally unrestrained configuration, the flap elastic members 60 effectively contract or gather the side flaps 58. The flap elastic members 60 can be secured to the side flaps 58 in an elastically contractible condition in at least two ways. For example, the flap elastic members 60 may be stretched and secured to the side flaps 58 while the side flaps 58 are in an uncontracted condition. Alternatively, the side flaps 58 may be contracted, for example by pleating, and the flap elastic members 60 secured to the contracted side flaps 58 while the flap elastic members 60 are in their unrelaxed or unstretched condition. The gasketing cuffs may alternatively comprise a number of different elastically extensible structures such as elastic nonwoven webs or foams; stretch laminates such as is described in U.S. Pat. No. 5,151,092 issued to Buell, et al. on Sep. 29, 1992, incorporated herein by reference; and structural elastic-like film (SELF) webs such as are described in U.S. Pat. No. 5,518,801 issued to Chappell, et al. on May 21, 1996, and incorporated herein by reference.

In the embodiment illustrated in FIG. 1, the flap elastic members 60 extend essentially the entire length of the side flaps 58 in the crotch region 26 of the diaper 20. Alternatively, the elastic members 60 may extend the entire length of diaper 20, or any other length suitable to provide a gasketing cuff. The length of the flap elastic members 60 is dictated by the diaper's design.

In the diaper 20 of FIG. 3, the flap elastic members 60 are associated with the side flaps 58 by securing them to the side flaps 58 with elastic attachment members 90. The elastic attachment members 90 should be flexible and of sufficient adhesiveness to hold the flap elastic member in its stretched condition. The elastic attachment members 90 herein are preferably glue beads or spirals made of hot melt adhesives such as marketed by ATO Findley Incorporated, Wauwatosa, Wis. as Findley 2511 or Findley H9254. It is recognized that traditional adhesives may not be compatible with all skin care compositions. Specifically, some skin care compositions may degrade the integrity of the adhesive bonds resulting in elastic creep and/or poor bond sufficiency. An adhesive which has been found especially effective in avoiding creep of elastics when a skin care composition is applied thereto is Findley H9254. A more detailed description of the manner in which the flap elastic members 60 may be positioned and secured to the diaper 20 can be found in U.S. Pat. No. 4,253,461 issued to Strickland and Visscher on Mar. 3, 1981, and U.S. Pat. No. 4,081,301 issued to Buell on Mar. 28, 1978, both of which are incorporated herein by reference.

One flap elastic member 60 which has been found to be suitable is an elastic strand made from natural rubber as available from Easthampton Rubber Thread Company of Stewart, Va., under the trademark L-1900 Rubber Compound. Other suitable flap elastic members 60 can be made from natural rubber, such as elastic tape sold under the trademark Fulflex 9211 by Fulflex Company of Scotland, N.C. An exemplary elastic member is a Lycra strand such as is available from DuPont Co. of Waynesboro, Va. under the designation Lycra-XA T-151. The flap elastic member 60 may also comprise any heat shrinkable elastic material as is well known in the art. Other suitable flap elastic members 60 may comprise a wide variety of materials as are well known in the art including elastomeric films, Lycra films or strands, polyurethane films, elastomeric foams, and formed elastic scrim.

In addition, the flap elastic members 60 may take a multitude of configurations. For example, the width of the flap elastic members 60 may be varied from about 0.25 mm (0.01 inches) to about 25 mm (1.0 inch) or more; the flap elastic members 60 may comprise a single strand of elastic material or may comprise several parallel or non-parallel strands of elastic material; or the flap elastic members 60 may be rectilinear or curvilinear. Still further, the flap elastic members 60 may be affixed to the diaper 20 in any of several ways which are well known in the art. For example, the flap elastic members 60 may be ultrasonically bonded, heat/pressure sealed into the diaper 20 using a variety of bonding patterns, or the flap elastic members 60 may simply be glued to the diaper 20.

The cuff may also comprise an elastic waist feature, such as an elasticized waistband (not shown), that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of these references being incorporated herein by reference, wherein a skin care composition is disposed thereon.

The cuff may further comprise elastic side panels that may be constructed in a number of configurations wherein a skin care composition is disposed thereon. Examples of diapers with elastic side panels are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; U.S. Pat. No. 5,151,092, issued to Buell et al. on Sep. 29, 1992; U.S. Pat. No. 5,580,411 issued to Nease, et al. on Dec. 3, 1996; U.S. Pat. No. 5,669,897 issued to LaVon, et al. on Sep. 23, 1997; and U.S. Pat. No. 5,569,232 issued to Roe, et al. on Oct. 29, 1996; each of which are incorporated herein by reference.

Embodiments of cuffs of the present invention may also include pockets for receiving and containing waste, spacers which provide voids for waste, barriers for limiting the movement of waste in the article, compartments or voids which accept and contain waste materials deposited in the diaper, and the like, or any combinations thereof wherein a skin care composition is disposed thereon. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al. on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996 entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,062,840, entitled "Disposable Diapers", issued to Holt et al. on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al. on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Pat. No. WO 94/14395 entitled "Absorbent Article Having An Upstanding Transverse Partition" published Jul. 7, 1994 in the name of Freeland, et al.; and U.S. 5,653,703 Absorbent Article Having Angular Upstanding Transverse Partition, issued Aug. 5, 1997 to Roe, et al. All of the above-cited references are hereby incorporated by reference herein.

Exemplary fastening systems 54 are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; U.S. Pat. No. 4,963,140 issued to Robertson et al. on Oct. 16, 1990; U.S. Pat. No. B1 4,662,875, issued to Hirotsu et al. on May 5, 1987; and U.S. Pat. No. 5,151,092, issued to Buell et al. on Sep. 29, 1992; each of which is incorporated herein by reference. A skin care composition may be disposed on one or more components of the fastening system to further enhance skin health. For example, a skin care composition as described herein may be disposed on the tape tabs to ease the effects of the tape tab chafing the skin.

Figure 4:
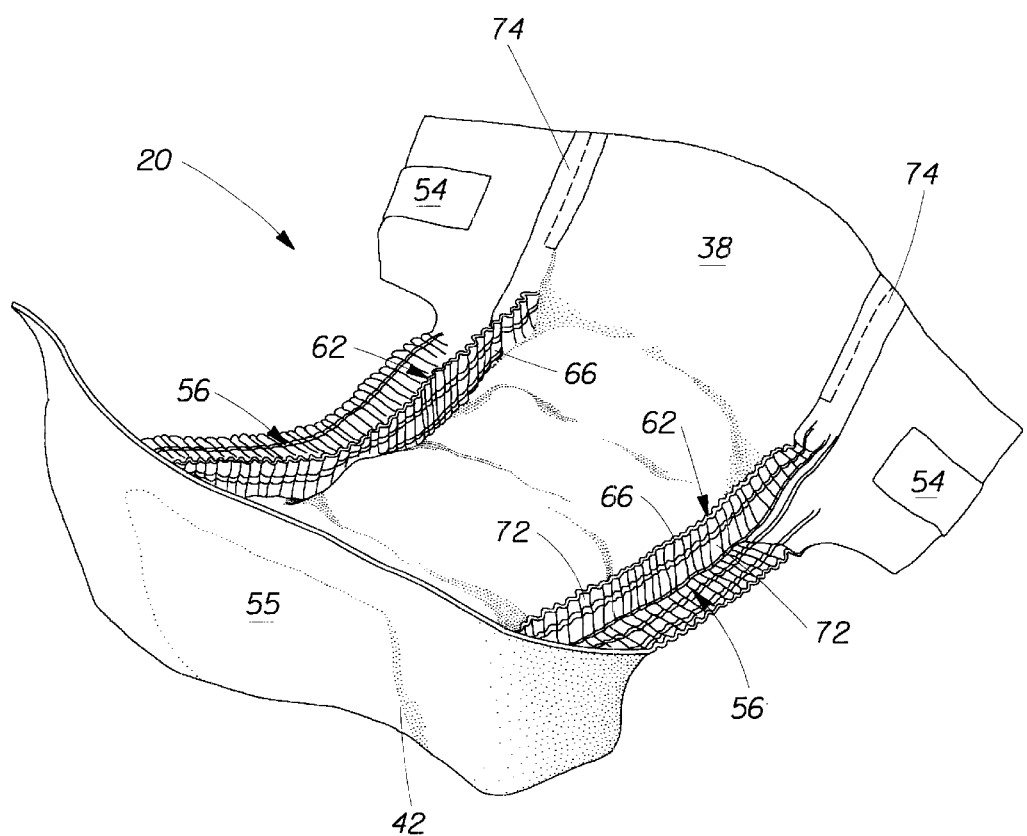
FIG. 4 is a perspective view of an absorbent article in the form of a disposable diaper according to the present invention

FIG. 4 is a perspective view of the diaper 20 in its elastically contracted position prior to being placed on the wearer. The topsheet 38 is shown as a portion of the body surface of the diaper 20, the backsheet 42 being disposed away from the body of the wearer. The gasketing cuffs 56 are shown to be gathered or contracted by the flap elastic members (not shown in FIG. 4). The diaper 20 is shown as having two barrier cuffs 62 extending adjacent to and inboard of the gasketing cuffs 56. The distal edges 66 are shown to be gathered and contracted by the spacing elastic members (not shown) in the crotch region. In addition, the ends 74 of the barrier cuff 62 are secured closed so as to provide comfort for the wearer, to obviate inversion of the barrier cuffs, and for ease of application of the diaper. A skin care composition 72 is disposed on the body surface of (applied to the body surface or applied to be migratable to the body surface of) each barrier cuff 62 so as to transfer to the skin of the wearer so as to provide the skin benefits discussed herein.

The diaper 20 is applied to a wearer by positioning the back waist region 24 under the wearer's back, and drawing the remainder of the diaper 20 between the wearer's leg so that the front waist region 22 is positioned across the front of the person. The ends of the tape-tab fasteners 54 are then secured preferably to the landing member 55 to close the diaper 20. In this manner, the barrier cuffs 62 should be disposed in the crotch region of the wearer and should provide the dispositions and functions described hereinbefore. Once applied, the distal edges 66 of the barrier cuffs 62 extend through the groin areas and diverge upwardly along both of the buttocks of the wearer. Neither of the barrier cuffs 62 encircle the thighs of the wearer. However, the gasketing cuffs 56 will encircle the thighs and create a gasketing action against the thighs. The barrier cuffs 62 contact the skin of the wearer and transfer the skin care composition 72 thereto to provide some or all of the benefits described herein.

The treated cuffs of the present invention are also useful in training pants or pull-on diapers. The term "training pants", as used herein, refers to disposable garments having fixed sides thereby defining a fixed waist opening and leg openings. Training pants are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993; U.S. Pat. No. 4,940,464 issued to Van Gompel, et al. on Jul. 10, 1990; and U.S. Pat. No. 5,092,861 issued to Nomura, et al. on Mar. 3, 1992 each of which is incorporated herein by reference. The treated cuffs of the present invention are also applicable to absorbent articles that are a combination or "hybrid" of training pants and diapers (pull-on diapers) as are described in U.S. Pat. No. 5,569,234, "Disposable Pull-On Pant" issued to Buell and Carlin on Oct. 29, 1996 incorporated herein by reference.

Another disposable absorbent article for which the treated cuffs of the present invention are useful are incontinence articles. The term "incontinence article" refers to pads, undergarments (pads held in place by a suspension system of some type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. Nos. 4,704,115; 4,909,802 issued to Ahr, et al.; U.S. Pat. No. 4,964,860 issued to Gipson, et al. on Oct. 23, 1990; and PCT Publication No. WO 92/11830, The Procter & Gamble Company, published on Jul. 23, 1992; each of which is incorporated herein by reference.

Figure 7:
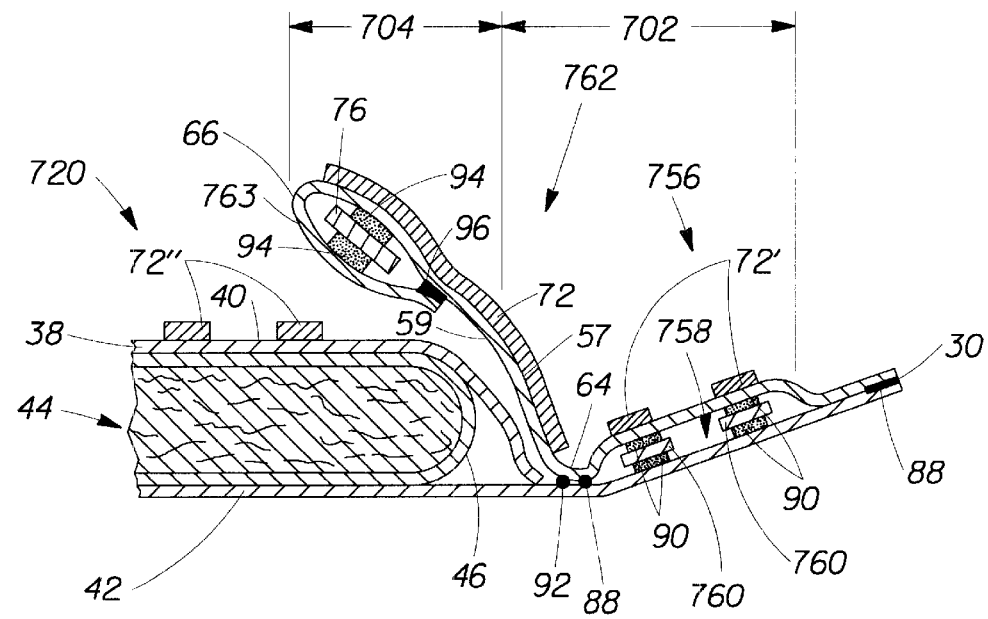
FIG. 7 is a fragmentary sectional view of an alternative embodiment of the present invention.

FIG. 7 is a simplified fragmentary sectional view of an alternative preferred diaper construction of the present invention. The diaper 720 comprises a chassis and treated cuffs joined to the chassis. The chassis comprises (i) an outer covering layer comprising a portion of the topsheet 38 and a portion of the backsheet 42, and (ii) the absorbent core 44. The cuffs each comprise a barrier cuff 762 and a gasketing cuff 756. The barrier cuff 762 comprises a separate barrier cuff member 763 having a flap portion 702 and a channel portion 704.

The flap portion 702 is formed by affixing portions of the barrier cuff member 763 to the backsheet 42 adjacent the longitudinal edge 30 of the diaper by flap attachment members 88, such as an adhesive; a leakage-resistant seal being formed by the flap attachment members 88, the flap portion 68, and the backsheet 42 to provide protection against leakage of liquids wicking along the topsheet 38. The flap portion 702 and the backsheet 42 define the side flap 758 of the gasketing cuff 756 and enclose the flap elastic members 760. The flap elastic members 760 are secured in the flap portion-backsheet-formed side flap 758 by elastic attachment members 90. The gasketing cuff 756 is thereby formed by the side flap 758 and the flap elastic members 760.

The channel portion 704 of the barrier cuff 762 is contiguous with the flap portion 702 and has a proximal edge 64 and a distal edge 66. The proximal edge 64 is preferably formed inboard of the gasketing cuff 756, more preferably between the side edge 46 of the absorbent core and the flap elastic member 760, by adjoining a segment of the barrier cuff member 763 to the backsheet 42 by the proximal securement member 92 such as a mechanical/pressure bond so as to form a leakage-resistant seal along the proximal edge 64 to present a barrier to liquid wicking through the topsheet 38 so as to prevent the liquids from wicking underneath the barrier cuffs to the edges of the diaper 20. The distal edge 66 is preferably disposed inboard of the proximal edge 64 and is not secured to any underlying elements of the diaper 20. As shown in FIG. 7, the distal edge 66 is preferably formed by folding the end of the barrier cuff member 763 back upon itself and securing it to another segment of the barrier cuff member by the distal attachment member 96 to form a tunnel. A spacing means such as a spacing elastic member 76 is enclosed in the tunnel; the spacing elastic member 76 being secured in the barrier cuff 762 by the elastic attachment members 94. (As an alternative embodiment, only the ends of the spacing elastic member are secured to the barrier cuff element to create a "drawstring elastic" such that the middle segment of the elastic "floats" in the tunnel. This drawstring elastic is described in more detail in U.S. Pat. No. 4,816,025 issued to Richardson on Mar. 28, 1989, which patent is incorporated herein by reference.) The distal edge 66 is thus spaced away from the body surface 40 of the topsheet 38 by the gathering action of the spacing elastic member 77.

In the embodiment shown, the topsheet 38 is positioned adjacent the body surface of the absorbent core 44 and extends beyond the side edge 46 of the absorbent core 44 but terminates inwardly of the proximal edge 64. (Alternatively, the topsheet may extend outwardly beyond the proximal edge but terminate inwardly of outermost flap attachment member 88 to obtain the benefits of the structure.) A more detailed description of the cuff construction of this embodiment is described in U.S. Pat. No. 4,795,454, "Absorbent Article Having Leakage-Resistant Dual Cuff", issued to Dragoo on Jan. 3, 1989, which patent is incorporated herein by reference.

The flap portion 702 is contiguous with the channel portion 704 and extends outwardly from the proximal edge 64 of the channel portion 704 toward the longitudinal edge 30, preferably to the longitudinal edge 30, such that the side flap 758 is formed from the extension of the backsheet 42 and the flap portion 702. While the flap portion 702 is preferably a continuous segment of the barrier cuff member 763, the flap portion 702 may be formed from a different piece of material secured to the channel portion 704 of the barrier cuff 762. Thus, the flap portion 702 may have different physical properties, dimensions, and characteristics than the channel portion 704. For example, the flap portion 702 need not be hydrophobic nor extend outwardly to the longitudinal edge 30. In addition, each of the barrier cuffs 762 need not have a flap portion such that a flap portion may be omitted entirely. The flap portion is, however, preferably hydrophobic, compliant, soft feeling and non-irritating to the wearer's skin since it contacts the legs of the wearer when in use.

An effective amount of a skin care composition is disposed on the cuff to provide skin care benefits for the wearer. To effectuate delivery of the skin care composition to the wearer's skin during use, it is preferred to dispose the skin care composition on the portions of the cuff that will contact the wearer's skin. Thus, the skin care composition may be disposed on both surfaces of the cuff, one surface of the cuff, or portions of either or both surfaces. In the embodiment shown in FIG. 7, the skin care composition may be disposed on the flap portion 702, the channel portion 704, or both. If a skin care composition is disposed on both the flap portion and the channel portion, the formulation of the skin care composition disposed on each need not be the same. In fact, each skin care composition may have different formulations and properties to provide different benefits. For example, a first skin care composition that, for example, reduces diaper rash may be disposed on the channel portion while a second skin care composition that, for example, reduces skin irritation and/or soothes the skin may be disposed on the flap portion. In the embodiment shown in FIG. 7, a first skin care composition 72 is disposed on the channel portion, preferably on the body surface thereof; a second skin care composition 72' is disposed on the flap portion, preferably on the body surface thereof; and a third skin care composition 72" is disposed on the topsheet, preferably on the body surface thereof. The formulation of each skin care composition need not be the same; however, in this particular embodiment, the formulation of each skin care composition is the same. Each skin care composition is disposed in an effective amount so as to transfer the skin care composition to the skin of the wearer.

As shown in FIG. 7, a skin care composition is preferably disposed on discrete portions of the flap portion and the channel portion. More preferably, the skin care composition is applied in one or more stripes, most preferably the stripe or stripes being aligned with those areas that overlie the flap elastic members or the spacing elastic members. The first skin care composition 72 is preferably applied to the channel portion 704 in a wide stripe (about 1.4 inch) extending from the distal edge 66 toward the proximal edge 64. The length of this stripe extends along a portion of the length of the spacing elastic member 76 (about 11.75 inch long) such that the portion of the barrier cuff element 763 adjacent the end of the spacing elastic member in the front waist region does not have the skin care composition 72 disposed thereon. (See, for example, FIG. 1.) A plurality of stripes of the second skin care composition 72' are disposed on the flap portion 702.

The skin care composition may be applied to the body surface 57 or the garment surface 59 of the barrier cuff member 763. If applied to the garment surface, the skin care composition preferably acts as a hydrophobic coating to assist in blocking the flow of urine and BM through the barrier cuffs. Also, the skin care composition is applied such that it will migrate or transfer through to the body surface of the barrier cuff member so as to be transferable onto the skin of the wearer and provide the skin care benefits discussed herein.

A skin care composition may also be disposed on the topsheet so as to provide a different benefit or the same benefit as that applied to the barrier cuff. An example of a skin care composition for a topsheet is described in U.S. Pat. No. 5,643,588 issued to Roe, et al. on Jul. 1, 1997, which patent is incorporated herein by reference.

Figure 8:
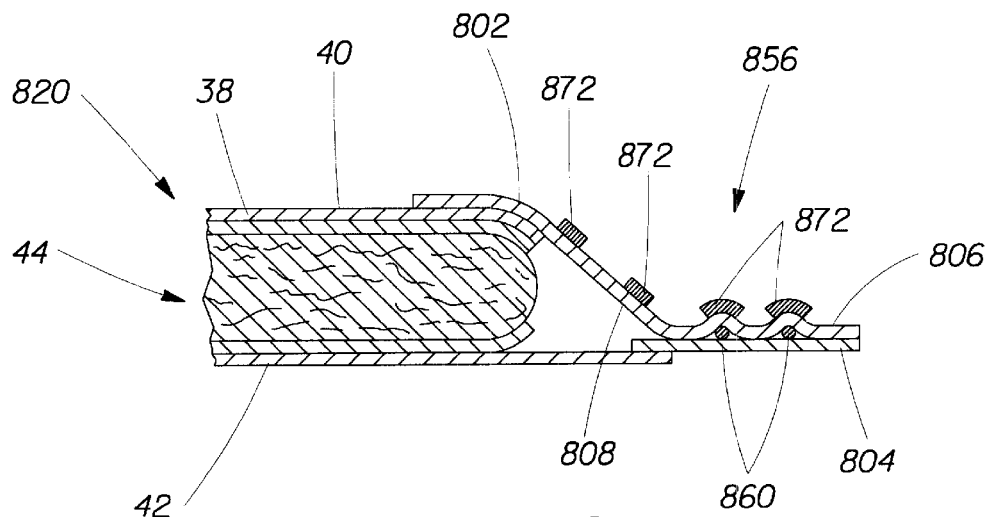
FIG. 8 is a cross-sectional view of a further alternative embodiment of the present invention.

FIG. 8 is another alternative embodiment of a treated cuff, particularly a breathable treated elastic leg cuff, of the present invention. As shown in FIG. 8, the diaper 820 comprises a chassis comprising an outer covering layer comprising a topsheet 38 and a backsheet 42, and an absorbent core 44 encased in the outer covering layer, preferably between the topsheet 38 and the backsheet 42. The leg cuff 856 comprises a side flap 858 and elastic members 860. The leg cuff 856 is formed as a separate unit that is joined to the chassis. In this particular embodiment, the side flap 858 comprises two cuff elements, a first cuff element 802 joined to the topsheet 38 and extending laterally outwardly therefrom and a second cuff element 804 joined to the backsheet 42 and extending laterally outwardly therefrom. The first cuff element 802 and the second cuff element 804 enclose the elastic members 860 which are operatively joined to either or both cuff elements to form a gasketing cuff. In the particular embodiment shown, each cuff element is formed of a material which allows the passage of vapor (breathes) while tending to retard the passage of liquid (air pervious but liquid impervious). In this particular embodiment, the cuff elements each comprise a nonwoven web; however, other breathable materials, including apertured formed films may be used. A more detailed description of such a leg cuff is disclosed in U.S. Pat. No. 4,636,207, issued to Buell on Jan. 13, 1987, which patent is incorporated herein by reference.

The skin care composition may be disposed on either the first cuff element, the second cuff element, or both. In a preferred embodiment as shown in FIG. 8, the skin care composition 872 is disposed on the first cuff element 802, preferably on the body surface 802, such that the skin care composition 872 may be readily transferred to the wearer's skin when the leg cuff 856 is in contact with the wearer. The skin care composition is preferably applied in one or more stripes with the stripe or stripes more preferably aligned with those areas that overlie the elastic members. Alternatively, the skin care composition may be applied to the garment surface 808 of the first cuff element 802 or to the second cuff element 804 and allowed to migrate or transfer through the materials to the body surface 806 of the first cuff element 802 to provide the benefits of the skin care composition as well as to provide a leg cuff that has reduced leakage. In addition, the skin care composition may be applied to the elastic members and allowed to transfer through to the body surface of the first cuff element. (In a further alternative embodiment, the second cuff element may be replaced by extending the backsheet all the way to the edge of the diaper).

The breathability (vapor permeability) of the cuff enhances the function of many of the skin care compositions used in the present invention by allowing vapor exchange within the diaper to reduce the relative humidity of the interior of the diaper. Excessive relative humidity in the absorbent article between the wearer's skin and the article can interfere with the normal transport of water vapor into and out of the skin. By providing a means for transport of such excess moisture (breathable cuffs), the driving force toward overhydration is reduced. This allows moisture adjacent the skin to be removed from the diaper, thereby further enhancing the skin health of the wearer over and above the reduction provided by the skin care composition of the present invention alone. (Disposable absorbent articles which provide improved protection against skin overhydration because of a skin care composition disposed on the topsheet, improved skin aeration such as is provided by improved breathability, and superior liquid handling performance is disclosed in U.S. patent application Ser. No. 08/926,566 "Disposable Absorbent Articles Providing A Skin Condition Benefit", Elder, et al. filed on Sep. 10, 1997, which is incorporated herein by reference.)

Figure 9:
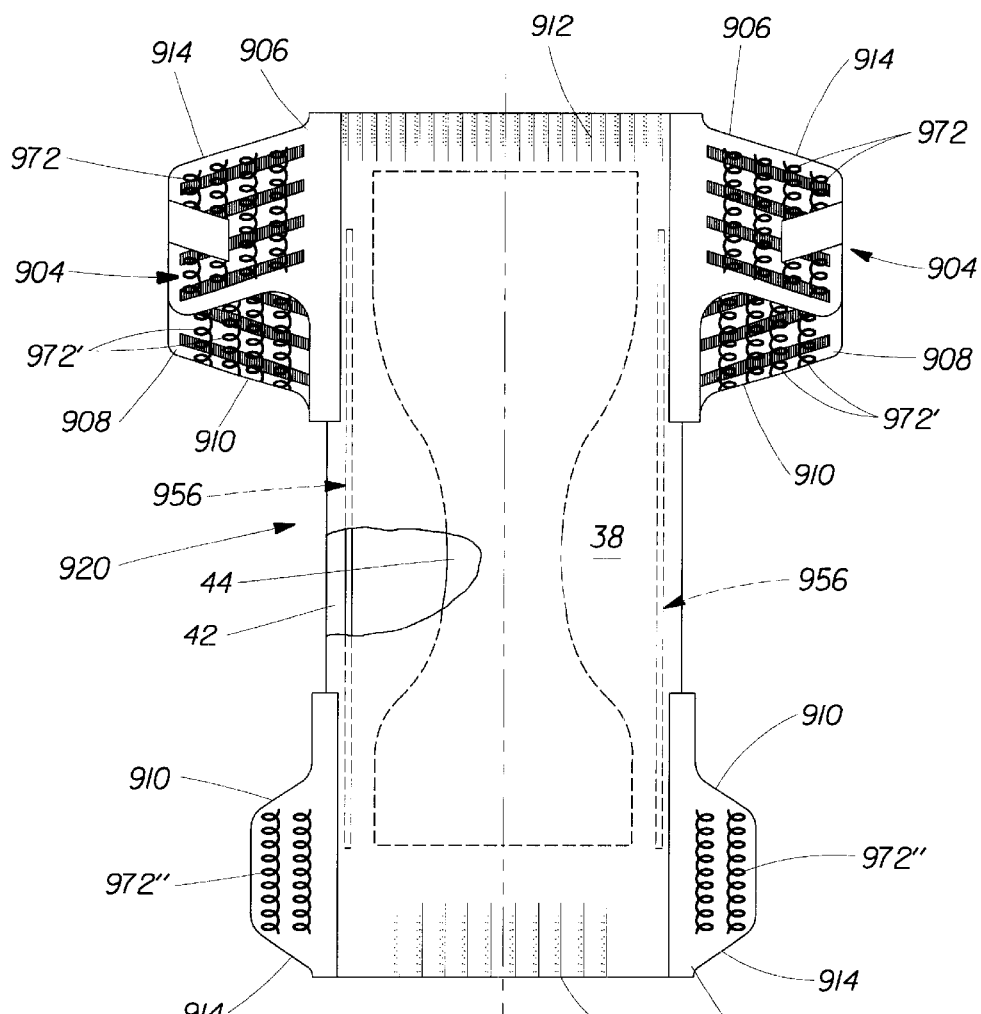
FIG. 9 is a plan view of a still further alternative embodiment of the present invention.
Figure 10:
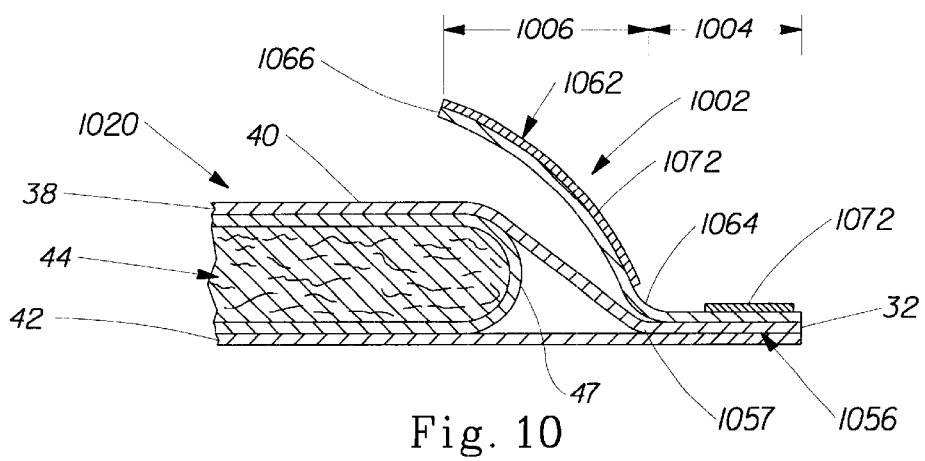
FIG. 10 is a fragmentary cross-sectional view of an even still further alternative embodiment of the present invention.

FIG. 9 is a plan view of a further alternative embodiment of the present invention having separate side panel laminates, front side panels 902 and back side panels 904, joined to the chassis (containment assembly). The extensible back side panels 904 have multi-directional stretch provided by a first side panel 906 and a second side panel 908 to provide separate extensibility along the waist and leg portions of the diaper 920. The side panels and the diaper are described more fully in U.S. Pat. No. 5,580,411, "Zero Scrap Method for Manufacturing Side Panels for Absorbent Articles" issued to Nease, et al. on Dec. 3, 1996 and U.S. application Ser. No. 08/115,048 entitled "Absorbent Article With Multi-Directional Extensible Side Panels", filed on Nov. 19, 1994 in the names of Robles, et al., which are incorporated herein by reference. The diaper 920 can have various treated cuffs and combinations thereof. The leg cuffs of the diaper 920 comprise the gasketing cuff 956 of the chassis (containment assembly) and the leg edges 910 of the second side panels 908 and of the front side panels 902. The waist cuffs comprise the elastic waistband 912 of the chassis (containment assembly) and the waist edge 914 of the first side panels 906 and the front side panels 902. In this embodiment, a skin care composition may be applied to the side panels or any portion thereof, to the gasketing cuff, to the elastic waistband, or any combination of the above. For example, a skin care composition may be applied to the elastic waistband and to a portion of the waist edge of each first side panel and front side panel. A skin care composition may be disposed on each leg cuff including a segment of the gasketing cuff, the leg edge of the second side panel and the leg edge of the front side panel. The skin care composition may thus provide a therapeutic or protective coating to the legs of the wearer. Alternatively, different formulation skin care compositions may be disposed on any combination or all of these cuffs. A further skin care composition may also be disposed on the topsheet 38 as described herein. As shown in FIG. 10, a first skin care composition 972 is disposed on the first side panel 906 in multiple stripes as spirals, a second skin care composition 972' is disposed on the second side panel 908 in multiple stripes as spirals, and a third skin care composition 972" is disposed on the front side panels 902 in multiple stripes as spirals. Each of the skin care compositions may be of the same formulation or different formulations. If the skin care compositions have different formulations, each particular skin care composition can be formulated to provide unique skin care benefits to different areas of the wearer.

FIG. 10 is a fragmentary sectional view of an alternative preferred diaper construction of a treated cuff disposed in the waist regions of a diaper. In particular, the drawing depicts a unitary waistcap/waistband. An exemplary embodiment of such a unitary waistcap/waistband is disclosed in U.S. Pat. No. 5,026,364 issued to Robertson on Jun. 25, 1991, which patent is incorporated herein by reference. (It should be noted that the present invention is not limited to unitary waistcap/waistbands but also encompasses waistbands such as shown in U.S. Pat. No. 4,515,595 issued to Kievit & Osterhage on May 7, 1985; as well as waistcaps such as disclosed in U.S. Pat. No. 4,738,677 issued to Foreman on April 19, 1988 and U.S. Pat. No. 4,743,246 issued to Lawson on May 10, 1988; each of these patents being incorporated herein by reference.) The unitary waistcap/waistband 1002 is formed by a single piece of elastomeric material operatively joined with the diaper 1020. The outward portion 1004 is operatively joined with the waist flap 1058 in an elastically contractible condition adjacent the end edge 32 of the diaper 1020 by a waistband securement member (not shown) such as ultrasonic bonds so as to form an elastic waistband 1056. The inward portion 1006 is contiguous with the outward portion 1004 and has a proximal edge 1064 and a distal edge 1066. The proximal edge 1064 of the inward portion 1006 is formed inboard of the end edge 32 of the diaper 1020, preferably between the waist edge 47 of the absorbent core 44 and the outward portion 1004, by joining a segment of the inward portion 1006 to the waist flap 1058 (the topsheet 38) by a proximal attachment member (not shown) such as an adhesive so as to form a seal along the proximal edge 1064. The distal edge 1066 is disposed inboard of the proximal edge 1064 and in the view shown, is not secured to any underlying elements of the diaper 1020, particularly the topsheet 38, so that portions of the inward portion 1006 may be spaced away from the body surface 40 of the topsheet 38 to form a waistcap 1062 (barrier cuff). In the embodiment shown, a single piece of material serves as both the elastic waistband 1056 and as the waistcap 1062 (barrier cuff). This single piece of material is referred to herein as a unitary waistcap/waistband 1002. The waistband enhances the fit of the diaper about the wearer and retards leakage from the waist area while the waistcap restrains, contains and holds body exudates within the diaper. However, it should be noted that separate elements may form both the waistcap and the waistband.

In the embodiment shown, a skin care composition may be disposed on the inward portion, the outward portion, or both. Thus, a skin care composition may be applied onto the waistcap or the waistband. The skin care composition is preferably applied to the body surface of the unitary waistcap/waistband so as to contact and transfer to the skin of the wearer during use. As shown in FIG. 10, a skin care composition 1072 is preferably disposed in one or more stripes on the body surface 1070 of the unitary waistcap/waistband 1002, more preferably adjacent the distal edge 1066 of the waistcap 1062 and in the waistband 1056. In order to enhance the hydrophobicity of the waistcap and to provide a skin care composition transferable to the skin, the skin care composition may alternatively be applied to the garment surface and allowed to migrate or transfer through to the body surface thereby providing a hydrophobic coating which helps retard the passage of liquid while allowing the skin care composition to be readily transferred to the skin of the wearer. In addition, a different formulation skin care composition may be applied to the inward portion versus the outward portion.

Another disposable absorbent article of the present invention are feminine hygiene articles, such as sanitary napkins. Suitable feminine hygiene articles are disclosed in U.S. Pat.

No. 4,556,146, issued to Swanson et al. on Dec. 3, 1985; U.S. Pat. No. B1 4,589,876, issued to Van Tilburg on Apr. 27, 1993; U.S. Pat. No. 4,687,478, issued to Van Tilburg on Aug. 18, 1997; U.S. Pat. No. 4,950,264, issued to Osborn, III on Aug. 21, 1990; U.S. Pat. No. 5,009,653, issued to Osborn, III on Apr. 23, 1991; U.S. Pat. No. 5,267,992, issued to Van Tilburg on Dec. 7, 1993; U.S. Pat. No. 5,389,094, issued to Lavash et al. on Feb. 14, 1995; U.S. Pat. No. 5,413,568, issued to Road et al. on May 9, 1995; U.S. Pat. No. 5,460,623, issued to Emenaker et al. on Oct. 24, 1995; U.S. Pat. No. 5,489,283, issued to Van Tilburg on Feb. 6, 1996; U.S. Pat. No. 5,569,231, issued to Emenaker et al. on Oct. 29, 1996; and U.S. Pat. No. 5,620,430, issued to Bamber on Apr. 15, 1997; each of which is incorporated herein by reference.

Figure 11:
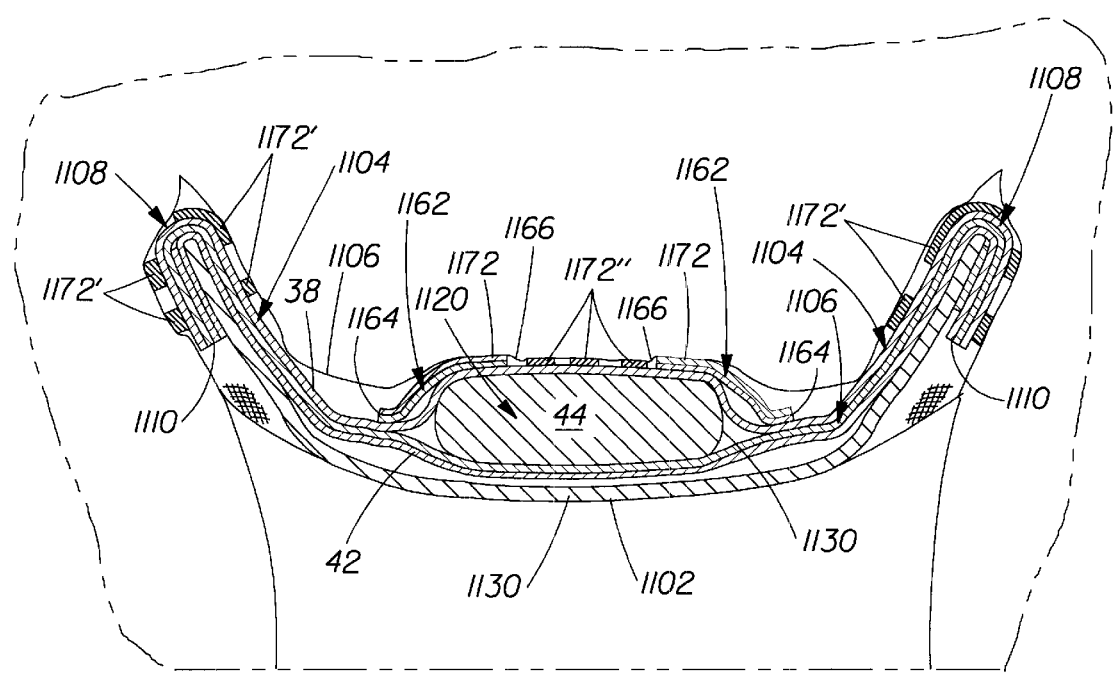
FIG. 11 is a fragmentary coronal view showing a sanitary napkin of the present invention and a panty in place on a user.

FIG. 11 shows a fragmentary coronal view showing a sectioned sanitary napkin 1120 having a treated cuff of the present invention positioned in a panty 1102 in place on a wearer during use. A more detailed description of a sanitary napkin having a barrier cuff is found in U.S. Pat. No. 5,649,917 issued to Roberts & Mancel on Jul. 22, 1997; which patent is incorporated herein by reference. As shown in FIG. 11, the sanitary napkin 1120 comprises a central absorbent pad comprising a topsheet 38, a backsheet 42, and an absorbent core 44 positioned between the topsheet 38 and the backsheet 42; a flap 1104 (commercially referred to as "wings" or "tabs") extending from each longitudinal edge 1130 of the central absorbent pad, each flap 1104 having at least one flexible axis, preferably a first axis of flexibility 1106 and a second axis of flexibility 1108 such that, in use, the elastic in the panty 1102 pushes the flaps 1104 adjacent the second axes of flexibility 1108 snugly against the body resulting in a double-wall barrier to contain menses; and a treated cuff comprising a barrier cuff 1162 (barrier means) having a proximal edge 1164 and a distal edge 1166, the proximal edge 1164 being joined to the napkin (preferably in this embodiment the flap 1104) to contain body exudates.

A skin care composition 1172 is disposed on each barrier cuff 1162 to provide skin care benefits as described herein. While the skin care composition may be applied to the entire cuff, one of the surfaces of the cuff, or any portions thereof, in the embodiment shown, the skin care composition is applied in one or more stripes to a portion of the body surface of the barrier cuff 1162 preferably adjacent the distal edge 1166. In addition, in the embodiment shown, a second skin care composition 1172' is also disposed on each flap 1104. A third skin care composition 1172" is disposed on the topsheet 38. The second skin care composition 1172' disposed on the flaps 1104 is preferably disposed on the portions of the flaps that come in contact with the wearer during use, typically the portions of the flaps adjacent the second axis of flexibility 1108. The second skin care composition 1172' may be disposed between the first axis of flexibility 1106 and the second axis of flexibility 1108 and/or between the second axis of flexibility 1108 and the distal edge 1110 of the flap, or both. The formulation of the skin care compositions applied to the barrier cuff, the topsheet, and the flaps can be different to provide different skin care benefits to different portions of the skin of the wearer. In the embodiment shown, the skin care compositions which are disposed on the topsheet, the flaps, and the barrier cuffs have the same formulation.

B. Skin Care Composition

While the specific skin care composition(s) delivered (referred to herein as "skin care composition" and "composition") in accordance with the present invention is an important factor in delivering desirable skin effects, it is preferred that the skin care composition should provide a protective, nonocclusive function (e.g., a relatively liquid impervious but vapor pervious barrier) to avoid skin hyperhydration and skin exposure to materials contained in body exudates; an abrasion minimizing function to reduce skin irritation in the areas where the cuffs contact the wearer's skin; or contain agents that deliver, either directly or indirectly, skin care benefits. For example, indirect benefits include improved removal of skin irritants such as feces or urine. The composition may be in a variety of forms, including, but not limited to, emulsions, lotions, creams, ointments, salves, powders, suspensions, encapsulations, gels, and the like.

As used herein, the term "effective amount of a skin care composition" refers to an amount of a particular composition which, when applied or migrated to ("disposed on") the body surface of a cuff, will be effective in reducing the abrasion between the cuff and skin in the areas where the cuffs contact the wearer's skin, providing a protective barrier and/or delivering a skin care benefit when delivered via cuffs, and/or reducing the adherence of BM to the skin. Unless otherwise indicated, the description pertaining to disposition of skin care composition on the cuffs will be applicable to compositions disposed on the topsheet, in such preferred embodiments. Of course, the effective amount of composition disposed on the cuff will depend, to a large extent, on the particular skin care composition used. Nonetheless, the quantity of the skin care composition disposed on at least a portion of the body surface of the cuff will preferably range from about 0.05 mg/in$^2$ (0.0078 mg/cm$^2$) to about 80 mg/in$^2$ (12 mg/cm$^2$), more preferably from about 1 mg/in$^2$ (0.16 mg/cm$^2$) to about 40 mg/in$^2$ (6 mg/cm$^2$), still more preferably from about 4 mg/in$^2$ (0.6 mg/cm$^2$) to about 26 mg/in$^2$ (4 mg/cm$^2$). These ranges are by way of illustration only and the skilled artisan will recognize that the nature of the composition will dictate the level that must be disposed thereon to achieve the desired skin benefits, and that such levels are ascertainable by routine experimentation in light of the present disclosure.

While the level of skin care composition disposed on the cuffs is an important aspect of the present invention, more important is the amount of composition transferred to the wearer's skin during use of one or more of the treated cuffs. Though the requisite level delivered to the skin to provide the desired skin benefits will depend to some degree on the nature of the composition employed, Applicants have found that relatively low levels may be delivered while still providing the desired skin effects. This is particularly true for preferred compositions, such as those described in the examples.

Another benefit of the present invention is the controlled application of the skin care composition to deliver the low but effective levels of composition required. This is in contrast to typically sporadic manual application of skin care agents, where the caregiver/user often applies significantly greater levels of material than are needed. Excessive materials added manually may adversely impact the fluid handling properties of the absorbent article, as a result of transfer from the skin to the article. Indeed, for certain materials, such as petrolatum, the levels applied manually may actually result in an occlusive effect, thereby compromising the skin. A benefit of the present invention is providing a barrier to surface moisture while avoiding occlusion of the skin (i.e., maintaining skin breathability). Thus, the present invention allows transfer of optimal levels of the composition to the skin to maintain and/or improve skin health.

With regard to the level of skin care composition that is transferred to the wearer during use of one treated absorbent article worn for a period of about 3 hours (a typical daytime wear time), particularly for preferred skin care compositions such as that described in Example 1, preferred is where at least about 0.01 mg/in$^2$ (0.0016 mg/cm$^2$), more preferably at least about 0.05 mg/in$^2$ (0.0078 mg/cm$^2$), still more preferably at least about 0.1 mg/in$^2$ (0.016 mg/cm$^2$), of the composition is transferred to the skin over a three hour wear period. Typically, the amount of composition delivered by one treated article will be from about 0.01 mg/in$^2$ (0.0016 mg/cm$^2$) to about 8 mg/in$^2$ (1.24 mg/cm$^2$), more preferably from about 0.05 mg/in$^2$ (0.0078 mg/cm$^2$) to about 6 mg/in$^2$ (0.93 mg/cm$^2$), still more preferably from about 0.1 mg/in$^2$ (0.016mg/cm$^2$)to about 5 mg/in$^2$ (0.78 mg/cm$^2$), over a three hour wear period.

It will be recognized that of the numerous materials useful in the skin care compositions delivered to skin in accordance with the present invention, those that have been deemed safe and effective skin care agents are logical materials for use herein. Such materials include Category I actives as defined by the U.S. Federal Food and Drug Administration's (FDA) Tentative Final Monograph on Skin Protectant Drug Products for Over-the-Counter Human Use (21 C.F.R. §347), which presently include: alantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Federal Food and Drug Administration's Tentative Final Monograph on Skin Protectant Drug Products for Over-the-Counter Human Use (21 C.F.R. §347), which presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, and the like. It will be recognized that one or more of these optional materials may be used in combination with other ingredients, such as those described herein.

As will be discussed hereinafter, the skin care compositions useful in the present invention preferably, though not necessarily, have a melting profile such that they are relatively immobile and localized on the wearer-contacting surface (body surface) of the cuff at room temperature, at least a portion of the composition will be transferable to the wearer at body temperature, and yet are not completely liquid under extreme storage conditions. Preferably, the compositions are easily transferable to the skin by way of normal contact, wearer motion, and/or body heat. Because the composition preferably is substantially immobilized on the cuffs wearer-contacting surface, relatively low levels of skin care composition are needed to impart the desired skin care benefits. In addition, special barrier or wrapping materials may be unnecessary in packaging the articles useful in the present invention.

In a preferred embodiment, the skin care compositions useful herein are solid, or more often semi-solid, at 20° C., i.e. at ambient temperatures. By "semisolid" is meant that the composition has a rheology typical of pseudoplastic or plastic liquids. When no shear is applied, the compositions can have the appearance of a semi-solid but can be made to flow as the shear rate is increased. This is due to the fact that, while the composition contains primarily solid components, it also includes some minor liquid components.

Preferably, the compositions of the present invention have a zero shear viscosity between about $1.0 \times 10^6$ centipoise and about $1.0 \times 10^8$ centipoise. More preferably, the zero shear viscosity is between about $5.0 \times 10^6$ centipoise and about $5.0 \times 10^7$ centipoise. As used herein the term "zero shear viscosity" refers to a viscosity measured at very low shear rates (e.g., 1.0 sec$^{-1}$) using plate and cone viscometer (a suitable instrument is available from TA Instruments of New Castle, Del. as model number CSL 100). One of skill in the art will recognize means other than high melting point components (as discussed below) can be used to provide comparable viscosities measured for such compositions comprising such means can be measured by extrapolating a plot of viscosity vs. shear rate for such compositions to a shear rate of zero at a temperature of about 20° C.

Preferred compositions are at least semi-solid at room temperature to minimize composition migration. In addition, the compositions preferably have a final melting point (100% liquid) above potential "stressful" storage conditions that can be greater than 45° C. (e.g., warehouse in Arizona, car trunk in Florida, etc.). Specifically, preferred compositions will have the following melt profile:

| Characteristic | Preferred Range | Most Preferred |
| --- | --- | --- |
| % liquid at room temp. (20° C.) | 2–50 | 3–25 |
| % liquid at body temp. (37° C.) | 25–95 | 30–90 |
| final melting point (° C.) | ≧38 | ≧45 |

By being solid or semisolid at ambient temperatures, preferred compositions do not have a tendency to flow and migrate to a significant degree to undesired locations of the absorbent article. This means less skin care composition is required for imparting desirable therapeutic, protective and/or conditioning benefits.

To enhance immobility of preferred compositions, the viscosity of the formulated compositions should be as high as possible to prevent flow from the cuff to undesired locations within the diaper. Unfortunately, in some instances, higher viscosities may inhibit transfer of composition to the wearer's skin or may be difficult to apply without processing problems. Therefore, a balance should be achieved so the viscosities are high enough to keep the compositions localized on the body surface of the cuff, but not so high as to impede transfer to the wearer's skin. Suitable viscosities for the compositions will typically range from about 1 to about 5000 centipoise, preferably from about 5 to about 300 centipoise, more preferably from about 5 to about 100 centipoise, measured at 60° C. using a rotational viscometer (a suitable viscometer is available from Lab Line Instruments, Inc. of Melrose Park, Ill. as Model 4537). The viscometer is operated at 60 rpm using a number 2 spindle.

For compositions designed to provide a skin care benefit, a useful active ingredient in these compositions is one or more skin protectants or emollients. As used herein, the term "emollient" is a material that protects against wetness or irritation, softens, soothes, supples, coats, lubricates, moisturizes, protects and/or cleanses the skin. (It will be recognized that several of the monographed actives listed above are "emollients", as that term is used herein.) In a preferred embodiment, these emollients will have either a plastic or liquid consistency at ambient temperatures, i.e., 20° C.

Representative emollients useful in the present invention include, but are not limited to, emollients that are petroleum-based; sucrose ester fatty acids; polyethylene glycol and derivatives thereof; humectants; fatty acid ester type; alkyl ethoxylate type; fatty acid ester ethoxylates; fatty alcohol type; polysiloxane type; propylene glycol and derivatives thereof; glycerine and derivatives thereof, including glyceride, acetoglycerides, and ethoxylated glycerides of $C_{12}$–$C_{28}$ fatty acids; triethylene glycol and derivatives thereof; spermaceti or other waxes; fatty acids; fatty alcohol ethers, particularly those having from 12 to 28 carbon atoms in their fatty chain, such as stearic acid; propoxylated fatty alcohols; other fatty esters of polyhydroxy alcohols; lanolin and its derivatives; kaolin and its derivatives; any of the monographed skin care agents listed above; or mixtures of these emollients.

Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for compositions of the present invention.

Suitable fatty acid ester type emollients include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$–$C_{28}$, preferably $C_{12}14\ C_{16}$) and shorter chain fatty acids e.g., lactic acid, such as lauryl lactate and cetyl lactate.

Suitable alkyl ethoxylate type emollients include $C_{12}$–$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). When employed, these alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$–$C_{22}$ fatty alcohols, preferably $C_{16}$–$C_{18}$ fatty alcohols. Representative examples include cetyl alcohol and stearyl alcohol, and mixtures thereof. When employed, these fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use herein include polysiloxane compounds. In general, suitable polysiloxane materials for use in the present invention include those having monomeric siloxane units of the following structure:

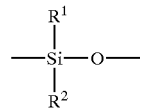

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the absorbent article. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the absorbent articles by such methods as, for example, emulsifying the polysiloxane in surfactant or providing the polysiloxane in solution with the aid of a solvent, such as hexane, listed for exemplary purposes only. Particular methods for applying polysiloxane emollients to absorbent articles are discussed in more detail hereinafter.

Preferred polysiloxanes compounds for use in the present invention are disclosed in U.S. Pat. No. 5,059,282 (Ampulski et al), issued Oct. 22, 1991, which is incorporated herein by reference. Particularly preferred polysiloxane compounds for use as emollients in the compositions of the present invention include phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane liquids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Suitable humectants include glycerine, propylene glycol, sorbitol, trihydroxy stearin, and the like.

When present, the amount of emollient that can be included in the composition will depend on a variety of factors, including the particular emollient involved, the skin benefits desired, the other components in the composition and like factors. The composition will comprise from 0 to about 100%, by total weight, of the emollient. Preferably, the composition will comprise from about 10 to about 95%, more preferably from about 20 to about 80%, and most preferably from about 40 to about 75%, by weight, of the emollient.

Another optional, but especially key component of certain skin care compositions useful in the present invention is an agent capable of immobilizing the composition (including the preferred emollient and/or other skin condition/protective agents) in the desired location in or on the treated cuff. Because certain of the preferred emollients in the composition have a plastic or liquid consistency at 20° C., they tend to flow or migrate, even when subjected to modest shear. When applied to a body surface or other location of a cuff, especially in a melted or molten state, the emollient will not remain primarily in or on the treated region. Instead, the emollient will tend to migrate and flow to undesired regions of the absorbent article.

Specifically, if the emollient migrates into the interior of the article, it can cause undesired effects on the absorbency of the absorbent core due to the hydrophobic characteristics of many of the emollients and other skin conditioning agents used in the compositions useful in the present invention. It also means that much more emollient has to be applied to the cuff to get the desired benefits. Increasing the level of emollient not only increases the cost, but also exacerbates the undesirable effect on the absorbency of the core and undesired transfer of composition during processing/converting of the treated cuffs.

The immobilizing agent counteracts this tendency of the emollient to migrate or flow by keeping the emollient primarily localized on the surface or in the region of the cuff to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier or dispersed therein), it entraps the emollient on the surface of the wearer contacting surface of the cuff or in the region to which it is applied.

It is also advantageous to "lock" the immobilizing agent on the wearer contacting surface or the region of the cuff to which it is applied. This can be accomplished by using immobilizing agents which quickly set up (i.e., solidify) upon application to the cuff. In addition, outside cooling of the treated cuff via blowers, fans, cold rolls, etc. can speed up crystallization of the immobilizing agent.

In addition to being miscible with (or solubilized in) the emollient, the immobilizing agent will preferably have a melting profile that will provide a composition that is solid or semisolid at ambient temperature. In this regard, preferred immobilizing agents will have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

When utilized, immobilizing agents useful herein can be selected from any of a number of agents, so long as the preferred properties of the skin care composition provide the skin benefits described herein. Preferred immobilizing agents will comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilizing agents include $C_{16}$–$C_{18}$ fatty alcohols, most preferably crystalline high melting materials selected from the group consisting of cetyl alcohol, stearyl alcohol, behenyl alcohol, and mixtures thereof. (The linear structure of these materials can speed up solidification on the treated cuff.) Mixtures of cetyl alcohol and stearyl alcohol are particularly preferred. Other preferred immobilizing agents include $C_{16}$–$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear. Importantly, these preferred immobilizing agents such as the $C_{16}$–$C_{18}$ fatty alcohols increase the rate of crystallization of the composition causing the composition to crystallize rapidly onto the surface of the substrate.

Other types of immobilizing agents that may be used herein include polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using cuffs to which the composition is applied, these esters and amides should also be relatively mild and non-irritating to the skin.

Suitable polyhydroxy fatty acid esters for use in the present invention will have the formula:

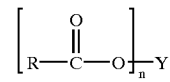

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri- esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di- esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters and diesters are particularly preferred and include sucrose mono- and di-stearate and sucrose mono- and di- laurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —$CH(CH_2OH)$—$[(CHOH)_{n-1}]$—$CH_2OH$, —$CH_2OH$—$CH_2$—$(CHOH)_2(CHOR^3)(CHOH)$—$CH_2OH$, where n is an integer from 3 to 5, and $R^3$ is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl. $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

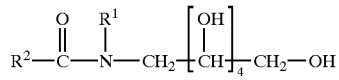

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents may require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, ozokerite, beeswax, candelilla, paraffin, ceresin, esparto, ouricuri, rezowax, isoparaffin, and other known mined and mineral waxes. The high melt point of these materials can help immobilize the composition on the desired surface or location on the cuff. Additionally microcrystalline waxes are effective immobilizing agents. Microcrystalline waxes can aid in "locking" up low molecular weight hydrocarbons within the skin care composition. Preferably the wax is a paraffin wax. An example of a particularly preferred alternate immobilizing agent is a paraffin wax such as Parrafin S.P. 434 from Strahl and Pitsch Inc. P.O. Box 1098 West Babylon, N.Y. 11704.

The amount of the optional immobilizing agent that can be included in the composition will depend on a variety of factors, including the actives (e.g., emollients) involved, the particular immobilizing agent involved, if any, the other components in the composition, whether an emulsifier is required to solubilize the immobilizing agent in the other components, and like factors. When present, the composition will typically comprise from about 5 to about 90% of the immobilizing agent. Preferably, the composition will comprise from about 5 to about 50%, most preferably from about 10 to about 40%, of the immobilizing agent.

Compositions can comprise other components typically present in emulsions, creams, ointment, lotions, powders, suspensions, etc. of this type. These components include water, viscosity modifiers, perfumes, disinfectant antibacterial actives, antiviral agents, vitamins, pharmaceutical actives, film formers, aloe vera, deodorants, opacifiers, astringents, solvents, preservatives, and the like. In addition, stabilizers can be added to enhance the shelf life of the composition such as cellulose derivatives, proteins and lecithin. All of these materials are well known in the art as additives for such formulations and can be employed in appropriate amounts in the compositions for use herein.

If water-based skin care compositions are used, a preservative will be needed. Suitable preservatives include propyl paraben, methyl paraben, benzyl alcohol, benzylkonnium, tribasic calcium phosphate, BHT, or acids such as citric, tartaric, maleic, lactic, malic, benzoic, salicylic, and the like. Suitable viscosity increasing agents include some of the agents described as effective immobilizing agents. Other suitable viscosity increasing agents include alkyl galactomannan, silica, talc, magnesium silicate, sorbitol, colloidal silicone dioxide, magnesium aluminum silicate, zinc stearate, wool wax alcohol, sorbiton, sesquioleate, cetyl hydroxy ethyl cellulose and other modified celluloses. Suitable solvents include propylene glycol, glycerine, cyclomethicone, polyethylene glycols, hexalene glycol, diol and multi-hydroxy based solvents. Suitable vitamins include A, D-3, E, B-5 and E acetate.

C. Application of Skin Care Composition to Cuffs (or Other Webs)

In preparing treated cuff products according to the present invention, the skin care composition is preferably applied to the body surface (i.e., wearer-contacting surface) of the cuff. However, since certain skin care compositions disclosed herein can penetrate or migrate through some of the cuff materials disclosed herein, the skin care composition may alternatively be applied to the garment surface of the cuff such that an effective amount of the skin care composition is disposed on the body surface. In fact, in some circumstances, this may be a preferred approach to achieve the benefits of a fully treated cuff (i.e., both sides are treated) though application is to one surface only.

Any of a variety of application methods that distribute lubricious materials having a molten or liquid consistency can be used to apply the skin care composition to the cuffs. Suitable application methods include coating (e.g., gravure or slot coating), spraying, printing (e.g., flexographic printing), extruding, or combinations of these or other application techniques (e.g. spraying the skin care composition on a rotating surface, such as a calendar roll, that then transfers via contact coating the skin care composition to the body surface of the diaper cuffs). If desired, the skin care composition can also be applied to both sides of the cuffs.

The manner of applying the skin care composition to the cuffs should be such that the cuffs do not become over saturated with the skin care composition. If the cuffs are treated with excessive amounts of the skin care composition, there is a greater potential for the skin care composition to migrate to undesired locations of the article, for example, into the interior of the article where it can have a detrimental effect on the absorbency of the underlying absorbent core. Also, saturation of the cuffs is not required to obtain the therapeutic and/or protective skin care composition benefits.

The minimum level of skin care composition to be applied to the cuff is the smallest amount effective in reducing erythema, diaper rash, red marking, skin irritation or other adverse skin conditions. (The compositions can also be effective in reducing the adherence of BM to the skin of the wearer.) Of course, the effective amount of a skin care composition will depend, to a large extent, on the particular skin care composition used. Because the emollient is substantially immobilized on the body surface of the cuff, less skin care composition is needed to impart the desired skin care benefits. Such relatively low levels of skin care composition are adequate to impart the desired therapeutic and/or protective skin care composition benefits to the cuff.

The skin care composition may be applied evenly and uniformly onto either or both surfaces of the cuff or portions thereof. The skin care composition may also be applied in a pattern (i.e., stripes, boxes, dots, spirals, etc.). Preferably, the skin care composition is registered with the region of the cuff that will, in use, be most in contact with the wearer. Most preferably, as described in the Examples hereinafter, the skin care composition is applied in a stripe to a discrete portion of the cuff, e.g., a 1.4 inch wide (diaper lateral direction, such that the distal edge of the cuff is covered) and 11.75 inch long (diaper longitudinal direction) patch generally disposed in the crotch portion of the body surface of the cuff.

The skin care composition can also be applied nonuniformly to either or both surfaces of the cuff. By "nonuniform", it is meant that the amount, pattern of distribution, etc., of the skin care composition can vary over the cuff surface. For example, some portions of the treated surface of the cuff can have greater or lesser amounts of skin care composition, including portions of the surface that do not have any skin care composition on it.

The skin care composition can be applied to the cuff or a web that forms a portion of the cuff at any point during assembly. For example, the skin care composition can be applied to the cuff of the finished product before it has been packaged. The skin care composition can also be applied to the cuff or the web before it is combined with the other raw materials to form a finished product, either at the converting site prior to combination with other article components or as a pretreated stock material.

The skin care composition is typically applied from a melt thereof to the cuff. Since the skin care composition melts at significantly above ambient temperatures, it is usually applied as a heated coating to the cuff. Typically, the skin care composition is heated to a temperature in the range from about 35° to about 100° C., preferably from 40° to about 90° C., prior to being applied to the cuff. Once the melted skin care composition has been applied to the cuff, it is allowed to cool and solidify to form a solidified coating or film disposed on the surface of the cuff. Preferably, the application process is designed to aid in the cooling/set up of the composition.

Figure 5:
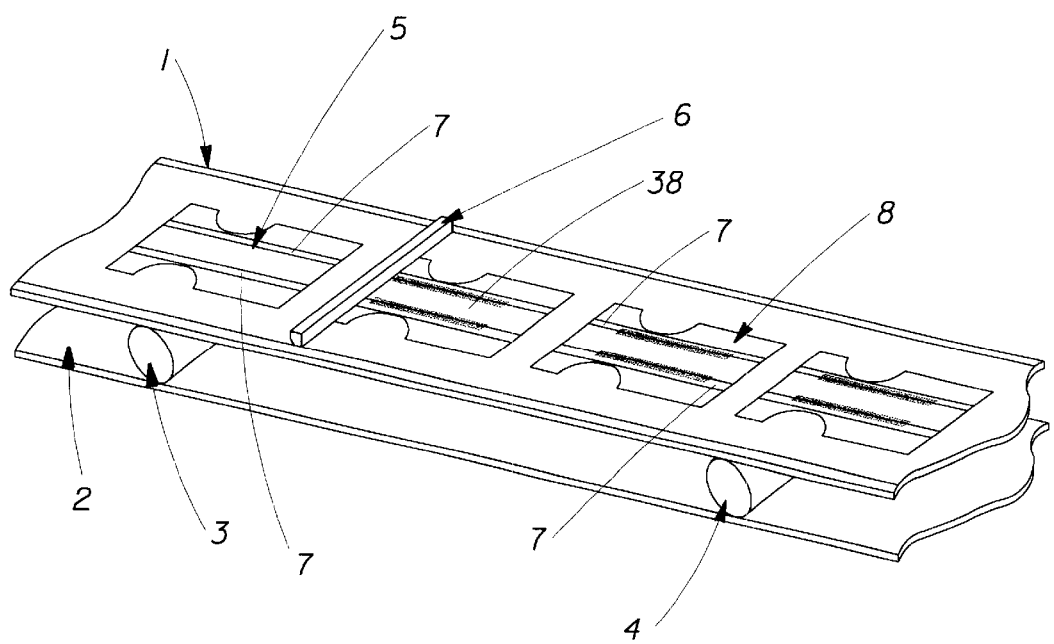
FIG. 5 is a schematic representation illustrating a preferred process for applying the composition of the present invention to diaper barrier cuffs.

In applying skin care compositions of the present invention to cuffs, slot coating, extrusion coating, gravure coating, and spraying methods are preferred. FIG. 5 illustrates a preferred method involving continuous or intermittent contact slot coating of the skin care composition on to a diaper barrier cuff during the converting operation. Referring to FIG. 5, conveyor belt 1 advances in the direction shown by the arrows on turning rolls 3 and 4 and becomes returning conveyor belt 2. Conveyor belt 1 carries nonlotioned diaper 5 to contact slot coating station 6 where the barrier cuff member 7 is coated with a hot, molten (e.g., 65° C.) skin care composition. After leaving slot coating station 6, the diaper 5 becomes diaper 8 having treated barrier cuffs. The amount of skin care composition transferred to barrier cuff member 7 is controlled by: (1) the rate at which the molten skin care composition is applied from contact slot coating station 6;

and/or (2) the speed at which conveyor belt 1 travels under slot coating station 6; and/or (3) positioning of the contact slot coating station. (If desired, the coating station may be positioned so as to coat the barrier cuff member 7 as well as portions of the topsheet 38 such that both the cuff and the topsheet have a skin care composition disposed thereon.)

Figure 6:
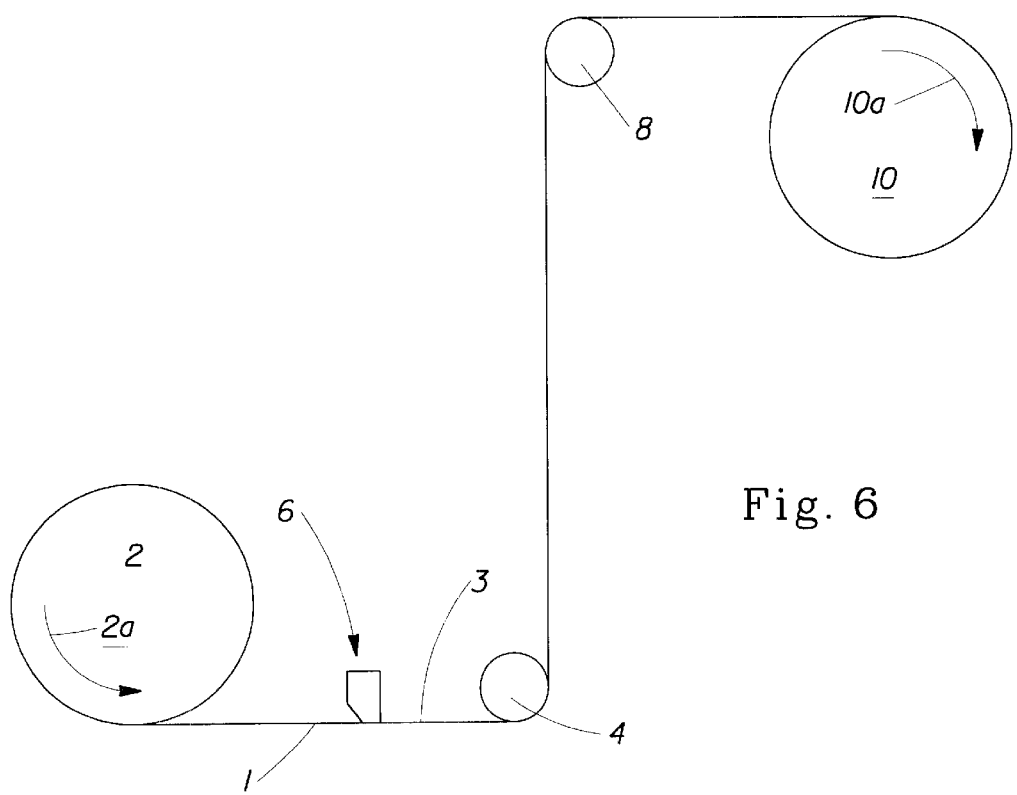
FIG. 6 is a schematic representation illustrating an alternative process for applying the composition of the present invention to diaper barrier cuffs.

FIG. 6 illustrates an alternate preferred method involving contact slot coating of the skin care composition on the diaper barrier cuffs before the cuffs are assembled with the other raw materials into a finished product. Referring to FIG. 6, a nonwoven barrier cuff web 1 is unwound from parent barrier cuff roll 2 (rotating in the direction indicated by arrow 2a) and advanced to the contact slot coating station 6 where one side of the web is coated with a hot, molten (e.g., 65° C.) skin care composition. After leaving slot coating station 6, nonwoven barrier cuff web 1 becomes a treated barrier cuff web indicated by 3. Treated barrier cuff web 3 is then advanced around turning roll 4 and turning roll 8, and then wound up on parent roll 10 (rotating in the direction indicated by arrow 10a). The treated web is then applied to the chassis of the diaper to form the barrier cuff member of the barrier cuff during the converting operation.

D. Skin Care Composition on Topsheet and Cuffs

As shown in FIG. 7, a first skin care composition may be disposed on the topsheet while a second skin care composition may be disposed on one or more of the cuffs. It has been found that the addition of a skin care composition to both the topsheet and the cuffs performs more effectively than either alone. The combination of a treated topsheet and treated cuffs provides a greater skin area to which the skin care composition may be transferred. With a larger area of the skin having the skin care composition transferred thereto, the better the likelihood that all parts of the wearer's skin will be maintained in a healthier state.

As discussed above, the first skin care composition and the second skin care composition can be the same formulation. However, it has been found that if the first skin care composition is different than the second skin care composition, then the diaper can be designed to deliver specific skin care benefits to specific portions of the skin of the wearer. For example, since the topsheet is typically in contact with the genitals and buttocks of the wearer during use, a first skin care composition specifically formulated to, for example, provide diaper rash prevention and/or treatment can be disposed on the topsheet. Since the cuffs tend to come in contact with the waist and legs of the wearer, the second skin care composition can be specifically formulated to, for example, provide reduced friction/red marking benefits. Thus, a specific portion of the diaper may have a specifically formulated skin care composition to target a specific area of the skin of the wearer for a skin care treatment or maintenance. This allows great flexibility in the design of the diapers and the ability of the manufacturer to provide specially designed products for a number of different consumer needs.

Another variation in the formulations of the skin care composition can result from the function of the elements on which the skin care composition is disposed. For example, the cuffs are typically designed to contain and restrain urine and runny BM within the diaper. It may be desired that the cuffs be hydrophobic, more particularly liquid impermeable, to prevent liquids from getting through the materials. If the skin care composition is also hydrophobic it can assist the cuff in resisting the passage of liquid through the cuff. In contrast, the topsheet needs to be highly liquid pervious to allow urine or menses to rapidly penetrate through the topsheet to the absorbent core. Placement of a hydrophobic skin care composition on the topsheet may degrade the performance of the topsheet. It may be more desirable to dispose a hydrophilic skin care composition on the topsheet to maintain the performance of the topsheet. Therefore, in some embodiments, it may be desirable that at least a portion of the skin care composition disposed on the topsheet be made of a hydrophilic material to promote rapid transfer of liquids (e.g., urine) through the topsheet. Similarly, it may be desirable that the skin care composition be sufficiently wettable to ensure that liquids will transfer through the topsheet rapidly. Alternatively, a hydrophobic skin care composition may be utilized, so long as they are applied such that the fluid handling properties of the topsheet are adequately maintained. For example, nonuniform application of the composition to the topsheet is one means to accomplish this goal. An example of nonuniform application is disclosed in U.S. patent application Ser. No. 08/908,852, "Diaper Having A Lotioned Topsheet", Roe, et al. filed on Aug. 8, 1997, which is incorporated herein by reference.

Where a hydrophilic composition is desired, depending upon the particular components used in the composition, a hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the C16–C18 fatty alcohols having HLB values below about 7 may require addition of hydrophilic surfactant to improve wettability when the composition is applied to the topsheet. Similarly, a hydrophobic emollient such as petrolatum may require the addition of a hydrophilic surfactant if hydrophilic composition is desired. Of course, the concern around wettability is not a factor when the wearer-contacting surface under consideration is desired to be hydrophobic or when fluid handling properties of the material is adequately maintained via other means (e.g., nonuniform application).

Suitable hydrophilic surfactants will preferably be miscible with the other components of the skin care composition so as to form blended mixtures. Because of possible skin sensitivity of those using disposable absorbent products to which the composition is applied, these surfactants should also be relatively mild and non-irritating to the skin. Typically, these hydrophilic surfactants are nonionic to be not only non-irritating to the skin, but also to avoid other undesirable effects on any other structures within the treated diaper. For example, reductions in tissue laminate tensile strength, adhesive bond sufficiencies, and the like.

Suitable nonionic surfactants may be substantially non-migratory after the composition is applied to the topsheet and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of disposable absorbent products, e.g., at least about 30° C. In this regard, these nonionic surfactants will preferably have melting points similar to those of the immobilizing agents previously described.

Suitable nonionic surfactants for use in compositions that will be applied to the topsheet include alkylglycosides; alkylglycoside ethers as described in U.S. Pat. No. 4,011,389 (Langdon, et al), issued Mar. 8, 1977, which is incorporated by reference; alkylpolyethoxylated esters such as Pegosperse 1000MS (available from Lonza, Inc., Fair Lawn, N.J.), ethoxylated sorbitan mono-, di- and/or tri- esters of C12–C18 fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of C11–C15 linear alcohols with 9 moles of ethylene oxide), marketed by Union Carbide Corporation; KYRO EOB (condensation product of C13–C15 linear alcohols with 9 moles of ethylene oxide), marketed by The Procter & Gamble Co., the NEODOL brand name surfactants marketed by Shell Chemical Co., in particular NEODOL 25-12 (condensation product of C12–C15 linear alcohols with 12 moles of ethylene oxide) and NEODOL 23-6.5T (condensation product of C12–C13 linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a C18 straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 72 (i.e., Steareth-2) and Brij 76 (i.e., Steareth-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the composition includes Aerosol OT, a dioctyl ester of sodium sulfosuccinic acid marketed by American Cyanamid Company.

Still another type of suitable surfactant for use in the composition includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the composition.

Where a hydrophilic composition is desired, the amount of hydrophilic surfactant required to increase the wettability of the composition to a desired level will depend in-part upon the HLB value and level of immobilizing agent, if any, used, the HLB value of the surfactant used and like factors. The composition can comprise from about 0.1 to about 50% of the hydrophilic surfactant when needed to increase the wettability properties of the composition. Preferably, the composition comprises from about 1 to about 25%, most preferably from about 10 to about 20%, of the hydrophilic surfactant when needed to increase wettability.

Applicants have discovered that maintaining or improving healthy skin under absorbent articles can be accomplished with repeated use, over a period of time (e.g., several days), of absorbent articles that are treated with two or more skin care compositions that are transferred to the wearer under normal usage conditions (e.g., contact, movement, handling by the caregiver after application of the article, body heat, etc.) such as the absorbent articles described herein. In this regard, a method for maintaining or improving skin health in the area covered by an absorbent article, comprises the steps of:

(a) applying to the wearer an absorbent article having a first skin care composition that provides a therapeutic and/or protective skin benefit upon transfer to the skin and a second skin care composition that provides a second skin benefit upon transfer to the skin;

(b) transferring to the wearer at least a portion of the first skin care composition and the second skin care composition during wear; and (c) repeating steps (a) and (b) with one or more additional articles with sufficient frequency to maintain or improve the health of the skin covered by the absorbent article relative to the skin covered by an equivalent absorbent article that does not comprise the first skin care composition and the second skin care composition, and without the need for manual application of skin protective agents (e.g., by the caregiver or wearer).

A key to this method is the use of an absorbent article having two or more skin care compositions and frequent cycles of cumulative delivery of a first skin care composition and a second skin care composition to the wearer's skin to maintain or improve skin health. Applicants have further discovered that delivery of relatively low levels of the compositions with each article wear are sufficient to obtain the skin benefits resulting from this novel method of cumulative delivery.

The article used in the present methods provides an available source from which the skin care compositions transfer onto the skin continuously over time. As the compositions are transferred, they accumulate on the skin surface to initiate and maintain protective activity. As a used article is discarded and replaced by a new one, this cycle is repeated for further composition accumulation above and beyond what a single or original article would have delivered on its own. Certain of the ingredients for use in preferred skin care compositions are known to penetrate the stratum corneum (e.g., petrolatum, which is preferred for use herein). Thus, even as some amount of the compositions are removed by cleaning, bathing, etc., or even if usage of treated articles as described herein is discontinued temporarily, some of the benefits of the skin compositions will remain with the user. As usage of treated articles is resumed before all of the benefits of the composition have dissipated, the user will derive benefits, in terms of reduced erythema and/or rash, more rapidly than would a user who has not used treated articles.

As indicated above, it is generally recognized that skin under absorbent articles is more susceptible to degradation of that skin's condition. Typically, cutaneous manifestations of these skin conditions include redness (also referred to as erythema) and/or rash. As such, Applicants describe herein a method for maintaining or improving skin health in regions covered by an absorbent article, wherein the desired endpoint of the method is the reduction or avoidance of erythema and/or rash when compared to skin covered by an equivalent absorbent article that does not comprise the skin care compositions.

Specific Illustrations of the Preparation of Treated Diaper Cuffs and Topsheets According to the Present Invention The following are specific illustrations of treating cuffs and/or topsheets or webs with skin care compositions in accordance with the present invention:

EXAMPLE 1

A. Preparation of Skin Care Composition

A skin care composition (Composition A) is made by mixing the following melted (i.e., liquid) components together: Petrolatum (available from Witco Corp., Greenwich, Conn. as Perfecta®) Stearyl Alcohol (available from The Procter & Gamble Company, Cincinnati, Ohio as CO1897) and aloe extract (available from Madis Botanicals, Inc., South Hackensack, N.J. as Veragel Lipoid in Kaydol). The weight percentages of these components are shown in Table I below:

TABLE I

| Component | Weight % |
| --- | --- |
| Petrolatum | 58 |
| Stearyl Alcohol | 41 |
| Aloe | 1 |

B. Preparation of Treated Diaper Leg Cuff by Hot Melt Coating

Skin care composition A is placed into a heated tank operating at a temperature of 170° F. The composition is subsequently applied with a contact applicator (i.e., a Meltex EP45 hot melt adhesive applicator head operating at a temperature of 170° F.) directly onto the body surface of the barrier cuffs of a diaper in a 1.4 inch wide (diaper lateral direction, such that the distal edge of the barrier cuff is covered) and 11.75 inch long (diaper longitudinal direction) area, the patch centered in the chassis in the longitudinal direction such that one or both ends of each spacing elastic member is covered by the skin care composition. Add-on level=0.0116 g/in$^2$ (18.0 g/m$^2$). The spacing elastic members is operatively joined to the barrier cuff member by a specially formulated adhesive to avoid creep such as Findley H9254 as discussed previously herein.

EXAMPLE 2

The skin care composition A (prepared in accordance with the procedure in Example 1) is subsequently applied onto the body surface of the barrier cuffs of a diaper in a 1.4 inch wide (diaper lateral direction, such that the distal edge of the barrier cuff is covered) stripe on each barrier cuff and extending the entire length of the barrier cuff. Add-on level=0.0116 g/in$^2$ (18 g/m$^2$).

EXAMPLE 3

The skin care composition A (prepared in accordance with the procedure in Example 1) is subsequently applied onto the body surface of the barrier cuffs of a diaper in a 1.4 inch wide (diaper lateral direction, such that the distal edge of the barrier cuff is covered) stripe on each barrier cuff and 8 inch long (diaper longitudinal direction) area, the patch centered in the contracted area of the barrier cuff such that each of the ends of the spacing elastic members is not covered by the skin care composition. Add-on level=0.0077 g/in$^2$ (12.0 g/m$^2$).

EXAMPLE 4

A. Preparation of Skin Care Composition

A water free skin care composition (Skin care composition B) is made by mixing the following melted (i.e., liquid) components together: Mineral Oil (Carnation White Mineral Oil, USP made by Witco Corp.); and Cetearyl Alcohol (a mixed linear $C_{16}$–$C_{18}$ primary alcohol made by The Procter & Gamble Company under the name TA-1618). The weight percentages of these components are shown in Table II below:

TABLE II

| Component | Weight % |
| --- | --- |
| Mineral Oil | 65 |
| Cetearyl Alcohol | 35 |

B. Preparation of Treated Leg Cuffs by Hot Melt Coating

Skin care composition B is placed into a heated tank operating at a temperature of 170° F. The composition is subsequently applied with a contact applicator (i.e., a Meltex EP45 hot melt adhesive applicator head operating at a temperature of 170° F.) onto the barrier cuffs of a diaper in a 1.4 inch wide (diaper lateral direction, such that the distal edge of the barrier cuff is covered) and 11.75 inch long (diaper longitudinal direction) area, the patch centered in the contracted area of the barrier cuff such that one or both ends of each spacing elastic member is covered by the skin care composition. Add-on level=0.0116 g/in$^2$ (18.0 g/m$^2$).

EXAMPLE 5

A. Preparation of Skin Care Composition

A water free skin care composition (Skin care composition C) is made by mixing the following melted (i.e., liquid) components together: Mineral Oil (Carnation White Mineral Oil, USP made by Witco Corp.); Cetearyl Alcohol (a mixed linear $C_{16}$–$C_{18}$ primary alcohol made by The Procter & Gamble Company under the name TA-1618); and Cetereath 10 (a $C_{16}$–$C_{18}$ linear alcohol ethoxylate having an average degree of ethoxylation of 10, made by ICI America). The weight percentages of these components are shown in Table III below:

TABLE III

| Component | Weight % |
| --- | --- |
| Mineral Oil | 50 |
| Cetearyl Alcohol | 35 |
| Ceteareth 10 | 15 |

B. Preparation of Treated Diaper by Hot Melt Coating

Skin care composition C is placed into a heated tank operating at a temperature of 170° F. The composition is subsequently applied with a contact applicator (i.e., a Meltex EP45 hot melt adhesive applicator head operating at a temperature of 170° F.) onto the barrier cuffs of a diaper in a 1.4 inch wide (diaper lateral direction, such that the distal edge of the barrier cuff is covered) and 11.75 inch long (diaper longitudinal direction) area, the patch centered in the contracted area of the barrier cuff such that one or both ends of each spacing elastic member is covered by the skin care composition. Add-on level=0.0116 g/in$^2$ (18.0 g/m$^2$).

EXAMPLE 6

A. Preparation of Skin care composition

A water free skin care composition (Skin care composition D) is made by mixing the following melted (i.e., liquid)

components together: Petrolatum (available from Witco Corp. as Perfecta®); Cetearyl Alcohol (a mixed linear $C_{16}$–$C_{18}$ primary alcohol made by The Procter & Gamble Company under the name TA-1618); Ceteareth 10 a $C_{16}$–$C_{18}$ linear alcohol ethoxylate having an average degree of ethoxylation of 10, made by ICI America; and Veragel 1:1 Lipoid with Kaydol (aloe extract in mineral oil made by Dr. Madis Laboratories, Inc.). The weight percentages of these components are shown in Table IV below:

TABLE IV

| Component | Weight % |
| --- | --- |
| Petrolatum | 49 |
| Stearyl Alcohol | 35 |
| Ceteareth 10 | 15 |
| Aloe | 1 |

B. Preparation of Treated Diaper by Hot Melt Coating

Skin care composition D is placed into a heated-tank operating at a temperature of 170° F. The composition is subsequently applied with a contact applicator (i.e., a Meltex EP45 hot melt adhesive applicator head operating at a temperature of 170° F.) onto the barrier cuffs of a diaper in a 1.4 inch wide (diaper lateral direction, such that the distal edge of the barrier cuff is covered) and 11.75 inch long (diaper longitudinal direction) area, the patch centered in the contracted area of the barrier cuff such that one or both ends of each spacing elastic member is covered by the skin care composition. Add-on level=0.0116 g/in$^2$ (18.0 g/m$^2$).

EXAMPLE 7

Composition A (made according Example 1) is placed into a heated tank operating at a temperature of 170° F. The composition is subsequently applied with a contact applicator (using, for example, a Meltex EP45 hot melt adhesive applicator head having 5 slots and operating at a temperature of 170° F.) onto the topsheet of an article in a striped pattern where the stripes run in the article's longitudinal direction. Specifically, 5 stripes are applied, each stripe measuring 0.25 in. wide (i.e., in the articles lateral direction) and 11.75 in. long at an add-on level=7.7 mg/in$^2$ (12 g/m$^2$, 1.19 mg/cm$^2$). The distance between the stripes is 0.31 in.

Skin care composition A is also subsequently applied onto the body surface of the barrier cuffs of an article in a 1.4 inch wide (lateral direction, such that the distal edge of the barrier cuff is covered) stripe on each barrier cuff and extending the entire length of the barrier cuff. Add-on level=0.0116 g/in$^2$ (18 g/m$^2$). Application is accomplished in the same manner as described in Example 1.

EXAMPLE 8

Composition D (made according Example 6) is placed into a heated tank operating at a temperature of 170° F. The composition is subsequently applied with a contact applicator (using, for example, a Meltex EP45 hot melt adhesive applicator head having a single slot and operating at a temperature of 170° F.) onto the topsheet of an article in generally uniform coating. Specifically, 1 stripe, measuring 2.5 in. wide (i.e., in the article's lateral direction) and 11.75 in. long, is applied at an add-on level=7.7 mg/in$^2$ (12 g/m$^2$, 1.19 mg/cm$^2$). The stripe is applied so as to be centered on the article's longitudinal centerline.

Skin care composition A is subsequently applied onto the body surface of the barrier cuffs of the article in a 1.4 inch wide (lateral direction, such that the distal edge of the barrier cuff is covered) stripe on each barrier cuff and extending the entire length of the barrier cuff. Add-on level=0.0116 g/in$^2$ (18 g/m$^2$). Application is accomplished in the same manner as described in Example 1.

What is claimed is:

1. An absorbent article to be worn by a wearer adjacent the skin, the absorbent article comprising:

a chassis comprising:
    a liquid pervious topsheet having a first surface and a second surface disposed opposite said first surface; and
    an absorbent core joined to said topsheet;

a cuff joined to said chassis, each said cuff having a first surface and a second surface disposed opposite said first surface;

an effective amount of a first skin care composition disposed on said cuff, said first skin care composition being semi-solid or solid at 20° C. and at least partially transferable to a wearer's skin; and an effective amount of a second skin care composition disposed on said topsheet, said second skin care composition being semi-solid or solid at 20° C. and at least partially transferable to a wearer's skin;

wherein the first skin care composition and the second skin care composition comprise:
    (i) from about 10% to about 95% of an emollient having a plastic or fluid consistency at 20° C.; and
    (ii) from about 5% to about 90% of a wax immobilizing agent capable of immobilizing said emollient on said topsheet and/or said cuff;

and wherein the first skin care composition is different from the second skin care composition in an element selected from the group consisting of formulation, add-on level, pattern, and combinations thereof.

2. The absorbent article of claim 1 wherein the wax immobilizing agent is selected from the group consisting of carnauba, ozokerite, beeswax, candelilla, paraffin, ceresin, esparto, ouricuri, rezowax, isoparaffin, and mixtures thereof.

* * * * *

UNITED STATES PATENT AND TRADEMARK OFFICE
CERTIFICATE OF CORRECTION

PATENT NO. : 6,476,288 B1
DATED : November 5, 2002
INVENTOR(S) : VanRijswijck et al.

It is certified that error appears in the above-identified patent and that said Letters Patent is hereby corrected as shown below:

Column 25,
Line 52, please delete "cuffs" and insert therefor -- cuff's --.

Column 27,
Line 35, please delete "$C_{12}14C_{16}$" and insert therefore -- $C_{12}$-$C_{16}$ --.

Column 41,
Line 20, after "heated", please delete "-" (the hyphen).

Signed and Sealed this

Twenty-eighth Day of September, 2004

JON W. DUDAS
*Director of the United States Patent and Trademark Office*